US010724034B2

(12) United States Patent
Derda et al.

(10) Patent No.: US 10,724,034 B2
(45) Date of Patent: Jul. 28, 2020

(54) GENETIC ENCODING OF CHEMICAL POST-TRANSLATIONAL MODIFICATION FOR PHAGE-DISPLAYED LIBRARIES

(71) Applicant: THE GOVERNORS OF THE UNIVERSITY OF ALBERTA, Edmonton (CA)

(72) Inventors: Ratmir Derda, Edmonton (CA); Pavel Kitov, Edmonton (CA); Simon Ng, Edmonton (CA); Katrina Felicia Tjhung, Calgary (CA); Daniel Ferrer Vinals, Edmonton (CA)

(*) Notice: Subject to any disclaimer, the term of this patent is extended or adjusted under 35 U.S.C. 154(b) by 0 days.

(21) Appl. No.: 15/520,958

(22) PCT Filed: Oct. 22, 2015

(86) PCT No.: PCT/CA2015/051077
§ 371 (c)(1),
(2) Date: Apr. 21, 2017

(87) PCT Pub. No.: WO2016/061695
PCT Pub. Date: Apr. 28, 2016

(65) Prior Publication Data

US 2017/0355982 A1 Dec. 14, 2017

Related U.S. Application Data

(60) Provisional application No. 62/067,183, filed on Oct. 22, 2014.

(51) Int. Cl.
*C40B 50/06* (2006.01)
*C12N 15/10* (2006.01)
*C40B 40/10* (2006.01)
*C40B 40/02* (2006.01)
*C40B 40/08* (2006.01)

(52) U.S. Cl.
CPC ....... *C12N 15/1082* (2013.01); *C12N 15/102* (2013.01); *C12N 15/1037* (2013.01); *C12N 15/1065* (2013.01); *C40B 40/02* (2013.01); *C40B 40/08* (2013.01); *C40B 40/10* (2013.01); *C40B 50/06* (2013.01)

(58) Field of Classification Search
None
See application file for complete search history.

(56) References Cited

U.S. PATENT DOCUMENTS

2015/0024958 A1* 1/2015 Derda ................ C12N 15/1037 506/9

FOREIGN PATENT DOCUMENTS

WO 2013/113127 A1 8/2013

OTHER PUBLICATIONS

Matochko et al. (2012) Methods vol. 58 pp. 47 to 55.*
International Search Report issued in corresponding PCT/CA2015/051077 dated Jan. 6, 2016; 10 pgs.

(Continued)

*Primary Examiner* — Christian C Boesen
(74) *Attorney, Agent, or Firm* — Bennett Jones LLP

(57) ABSTRACT

The present application provides a method of synthesizing a genetically-encoded chemical modification of a peptide library. A vector in a substrate, such as a phage, is modified to include a peptide linker and a modification to form a genetic "barcode". The barcode is screened against potential targets which may be used in drug discovery.

14 Claims, 29 Drawing Sheets

Specification includes a Sequence Listing.

a) peptide + modification; encode the peptide; encode the modification; M13 phage; 1. Pan 2. Sequence; decode the peptide; decode the modification; phage DNA; chemically-modified peptide hits b) linker; GlyGlyGly; variable sequence; (GGA)$_3$ (NNK)$_7$; cPTM #1; (GGC)$_3$ (NNK)$_7$; cPTM #2; Mix; $(6)^3$ = 216 combinations of codons for GlyGlyGly; cPTM #3; cPTM #216; 216 chemically post-translationally modified peptide libraries

(56) References Cited

OTHER PUBLICATIONS

Ng et al., "Quantitative synthesis of genetically encoded glycopeptide libraries displayed on M13 phage". ACS Chemical Biology, Jun. 24, 2012 (Jun. 24, 2012), vol. 7, pp. 1482-1487, ISSN 1554-8929.
Chen et al., "Peptide ligands stabilized by small molecules". Angewandte Chemie International Edition, Feb. 1, 2014 (Feb. 1, 2014), vol. 53, Issue 6, pp. 1602-1606, ISSN 1521-3773.
Ng et al, "Genetically encoded fragment-based discovery of glycopeptide ligands for carbohydrate-binding proteins". Journal of the American Chemical Society, Apr. 10, 2015 (Apr. 10, 2015), vol. 137, pp. 5248-5251, ISSN0002-7863, 4 pgs.
International Preliminary Report on Patentability dated May 4, 2017, in connection with corresponding International Application No. PCT/CA2015/051077 (7 pgs.).

* cited by examiner $$f = \frac{1}{3}\sum_{i=1}^{3}\frac{(n_i+1)}{^{tot}N_i}$$

FIGURE 6

Hidden Barcode (Carbonic Anhydrase)

| Sequence | Peptide | Carbonic | | | Blank | | | Naive | | | Bulk amplified | | | Ratio | | |
|---|---|---|---|---|---|---|---|---|---|---|---|---|---|---|---|---|
| AGTTGGTATAAGTTGGGAGGAGGA | SA---WYKL | 862 | 1159 | 285 | 0 | 0 | 0 | 3 | 5 | 0 | 5 | 3 | 11 | 2562 | 288 | 121 |
| AGTTGGCAGCAGCAGGGAGGAGGA | SA---WQQQ | 403 | 422 | 596 | 0 | 0 | 0 | 3 | 5 | 0 | 7 | 6 | 1 | 1579 | 178 | 102 |
| AGTTGGATTGTTCCTGGAGGAGGA | SA---WIVP | 449 | 190 | 324 | 0 | 0 | 0 | 0 | 0 | 0 | 2 | 1 | 0 | 1070 | 1070 | 321 |
| AGTTGGAATACGAAGGGAGGAGGA | SA---WNTK | 121 | 256 | 228 | 0 | 0 | 0 | 0 | 23 | 9 | 7 | 7 | 2 | 672 | 19 | 38 |
| AGTTATCAGTATAGTGGAGGAGGA | SA---YQYS | 154 | 194 | 51 | 0 | 0 | 0 | 0 | 0 | 9 | 1 | 6 | 2 | 443 | 44 | 44 |
| AGTTATGGTACGCATGGAGGAGGA | SA---YGTH | 50 | 118 | 63 | 0 | 0 | 0 | 0 | 9 | 0 | 6 | 14 | 13 | 257 | 26 | 7 |
| AGTACGGCGTTTATTGGAGGAGGA | SA---TAFI | 44 | 58 | 48 | 0 | 0 | 0 | 0 | 0 | 0 | 0 | 0 | 2 | 167 | 167 | 75 |
| AGTTGGACTTCTGGGGGAGGAGGA | SA---WTSG | 63 | 30 | 46 | 0 | 0 | 0 | 0 | 9 | 6 | 2 | 3 | 8 | 154 | 9 | 11 |
| AGTTATATGTCTAATGGAGGAGGA | SA---YMSN | 51 | 25 | 53 | 0 | 0 | 0 | 0 | 0 | 0 | 1 | 7 | 5 | 143 | 143 | 10 |
| AGTTGGACTTGGTTGGGAGGAGGA | SA---WTWL | 43 | 57 | 26 | 0 | 0 | 0 | 0 | 0 | 0 | 3 | 2 | 1 | 140 | 140 | 21 |
| AGTCAGATTGAGCATGGAGGAGGA | SA---QIEH | 35 | 20 | 27 | 0 | 0 | 0 | 9 | 18 | 0 | 9 | 15 | 12 | 91 | 3 | 2 |
| AGTTGGACGTATTGGGGAGGAGGA | SA---WTYW | 18 | 33 | 15 | 0 | 0 | 0 | 12 | 0 | 0 | 1 | 7 | 0 | 73 | 6 | 8 |
| AGTTGGCCGCCTTATGGAGGAGGA | SA---WPPY | 17 | 16 | 20 | 0 | 0 | 0 | 6 | 0 | 6 | 3 | 5 | 2 | 59 | 4 | 5 |
| AGTTGGCCGCCTCCGGGAGGAGGA | SA---WPPP | 10 | 10 | 15 | 0 | 0 | 0 | 6 | 0 | 0 | 0 | 0 | 1 | 39 | 6 | 35 |
| AGTTGGATTGTTCCAGGAGGAGGA | SA---WIVP | 9 | 6 | 9 | 0 | 0 | 0 | 0 | 0 | 0 | 0 | 0 | 0 | 27 | 27 | 27 |
| AGTTGGCTGGTGCTTGGAGGAGGA | SA---WLVL | 4 | 4 | 3 | 0 | 0 | 0 | 0 | 0 | 0 | 0 | 0 | 0 | 12 | 12 | 12 |
| AGTTGGTTTAAGTTGGGAGGAGGA | SA---WFKL | 3 | 5 | 2 | 0 | 0 | 0 | 0 | 0 | 0 | 0 | 0 | 0 | 11 | 11 | 11 |
| AGTTGGAAGCAGCAGGGAGGAGGA | SA---WKQQ | 3 | 2 | 4 | 0 | 0 | 0 | 0 | 0 | 0 | 0 | 0 | 0 | 10 | 10 | 10 |
| AGTTGGAGTGTTATGGGAGGAGGA | SA---WSVM | 3 | 2 | 4 | 0 | 0 | 0 | 0 | 0 | 0 | 0 | 0 | 0 | 10 | 10 | 10 |
| AGTTGGAATTCGAAGGGAGGAGGA | SA---WNSK | 3 | 4 | 2 | 0 | 0 | 0 | 0 | 0 | 0 | 0 | 0 | 0 | 10 | 10 | 10 |

B.

Hidden Barcode (Streptavadin)

| Sequence | Peptide | Streptavadin | | | Blank | | | Naive | | | Bulk amplified | | | Ratio | | |
|---|---|---|---|---|---|---|---|---|---|---|---|---|---|---|---|---|
| TCTCCGCAGATGTCTGGCGGTGGC | Bio--PQMS | 282 | 248 | 453 | 0 | 0 | 0 | 3 | 9 | 12 | 4 | 1 | 0 | 1092 | 41 | 197 |
| TCTGCGCATCCTTTGGGCGGTGGC | Bio--AHPL | 382 | 113 | 333 | 0 | 0 | 0 | 6 | 0 | 0 | 3 | 2 | 1 | 920 | 138 | 138 |
| TCTGGTTATACGCAGGGCGGTGGC | Bio--GYTQ | 240 | 227 | 147 | 0 | 0 | 0 | 0 | 9 | 0 | 0 | 1 | 0 | 682 | 68 | 614 |
| TCTCATTTTACGAATGGCGGTGGC | Bio--HFTN | 246 | 135 | 98 | 0 | 0 | 0 | 0 | 0 | 0 | 2 | 0 | 5 | 532 | 532 | 68 |
| TCTCCTACTCATACTGGCGGTGGC | Bio--PTHT | 154 | 178 | 118 | 0 | 0 | 0 | 6 | 0 | 0 | 2 | 5 | 0 | 500 | 75 | 64 |
| TCTCCGTCGATTGGTGGCGGTGGC | Bio--PSIG | 145 | 125 | 174 | 0 | 0 | 0 | 15 | 0 | 6 | 6 | 2 | 0 | 493 | 21 | 56 |
| TCTCCGGCGCTTCCTGGCGGTGGC | Bio--PALP | 125 | 108 | 210 | 0 | 0 | 0 | 0 | 0 | 0 | 1 | 2 | 2 | 492 | 492 | 89 |
| TCTCATCCGAGTTATGGCGGTGGC | Bio--HPSY | 85 | 214 | 104 | 0 | 0 | 0 | 0 | 0 | 6 | 0 | 7 | 0 | 448 | 67 | 58 |
| TCTTGGTATCCTCATGGCGGTGGC | Bio--WYPH | 85 | 150 | 127 | 0 | 0 | 0 | 0 | 0 | 3 | 4 | 0 | 1 | 402 | 121 | 72 |
| TCTCATTTGAGGGTTGGCGGTGGC | Bio--HLRV | 58 | 110 | 168 | 0 | 0 | 0 | 0 | 0 | 0 | 1 | 5 | 0 | 373 | 373 | 56 |
| TCTCATATGCCGCGTGGCGGTGGC | Bio--HMPR | 118 | 121 | 71 | 0 | 0 | 0 | 0 | 0 | 6 | 5 | 1 | 1 | 344 | 52 | 44 |
| TCTCCTGTTTCGATTGGCGGTGGC | Bio--PVSI | 75 | 94 | 128 | 0 | 0 | 0 | 0 | 0 | 6 | 4 | 0 | 0 | 330 | 49 | 74 |
| TCTTATATGAATAATGGCGGTGGC | Bio--YMNN | 110 | 134 | 40 | 0 | 0 | 0 | 9 | 0 | 3 | 2 | 0 | 0 | 316 | 24 | 142 |
| TCTCATAAGCTGAATGGCGGTGGC | Bio--HKLN | 95 | 98 | 72 | 0 | 0 | 0 | 0 | 0 | 3 | 0 | 11 | 11 | 294 | 88 | 12 |
| TCTCCTCATCTGCCTGGCGGTGGC | Bio--PHLP | 84 | 37 | 123 | 0 | 0 | 0 | 6 | 5 | 6 | 8 | 6 | 2 | 271 | 14 | 15 |
| TCTCCTCATTATAATGGCGGTGGC | Bio--PHYN | 53 | 110 | 70 | 0 | 0 | 0 | 6 | 5 | 0 | 2 | 2 | 0 | 259 | 21 | 58 |
| TCTCCTCTGGCGCAGGGCGGTGGC | Bio--PLAQ | 110 | 71 | 50 | 0 | 0 | 0 | 6 | 0 | 0 | 7 | 0 | 0 | 257 | 38 | 33 |
| TCTGTGCATGCGTGGGGCGGTGGC | Bio--VHAW | 73 | 39 | 119 | 0 | 0 | 0 | 0 | 0 | 0 | 4 | 0 | 2 | 257 | 257 | 38 |
| TCTGTGCATAATACTGGCGGTGGC | Bio--VHNT | 29 | 87 | 110 | 0 | 0 | 0 | 0 | 0 | 3 | 2 | 0 | 1 | 251 | 75 | 75 |
| TCTCCTTTTGTGCAGGGCGGTGGC | Bio--PFVQ | 82 | 61 | 54 | 0 | 0 | 0 | 0 | 0 | 0 | 0 | 0 | 2 | 219 | 219 | 99 |

FIGURE 10A
SA-WYKL
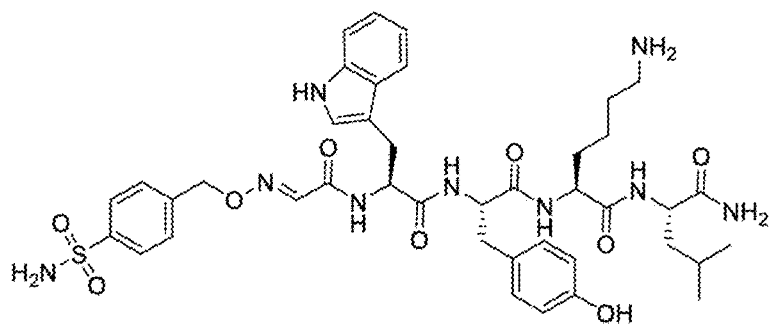
High resolution ESI MS: Calcd for C41H54N9O9S ([M+H]+) 848.376; found 848.3752.
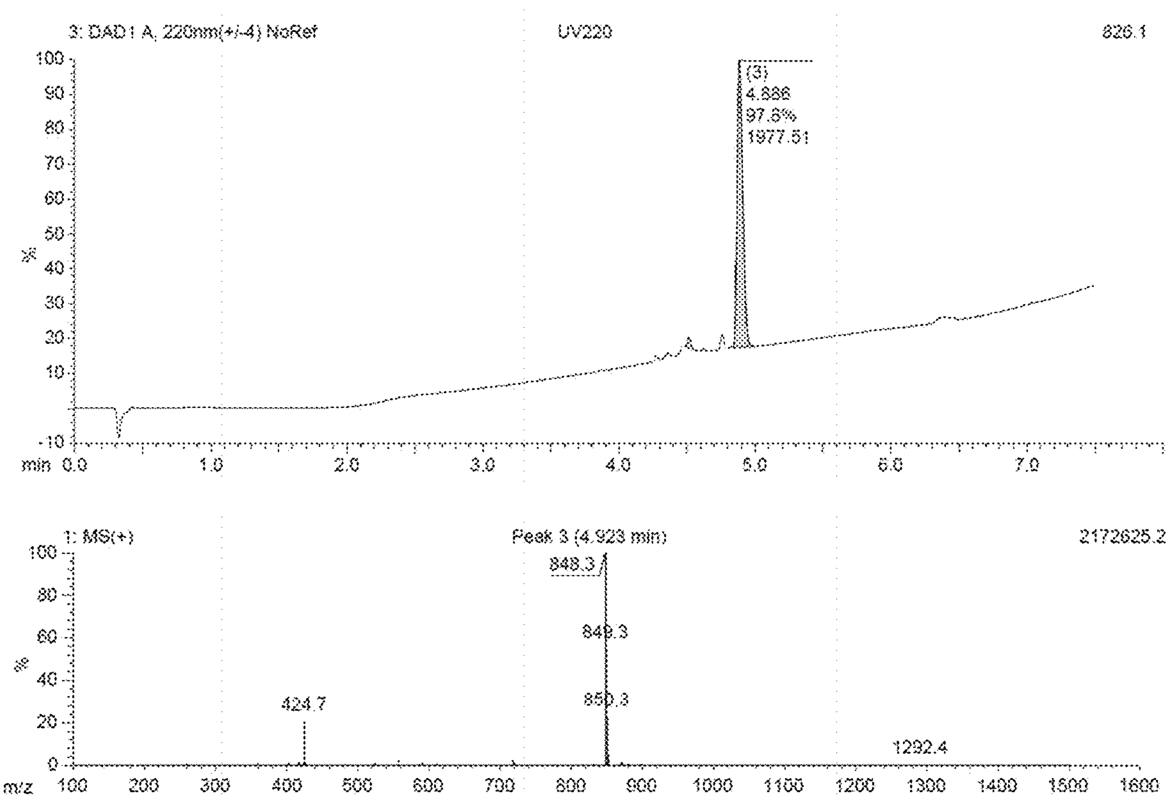

FIGURE 10B
SA-WQQQ
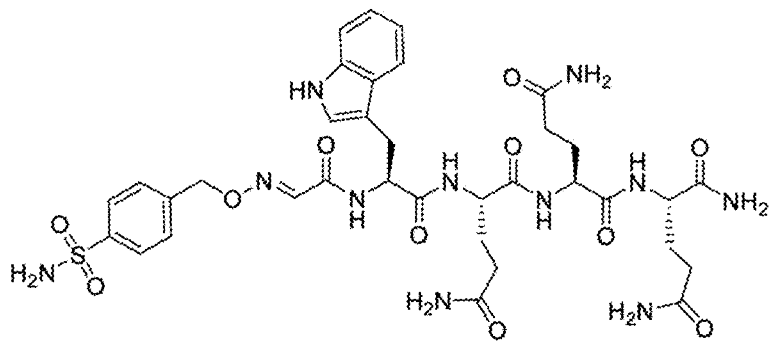
High resolution ESI MS: Calcd for C35H46N11O11S ([M+H]+) 828.3093; found 828.3099.
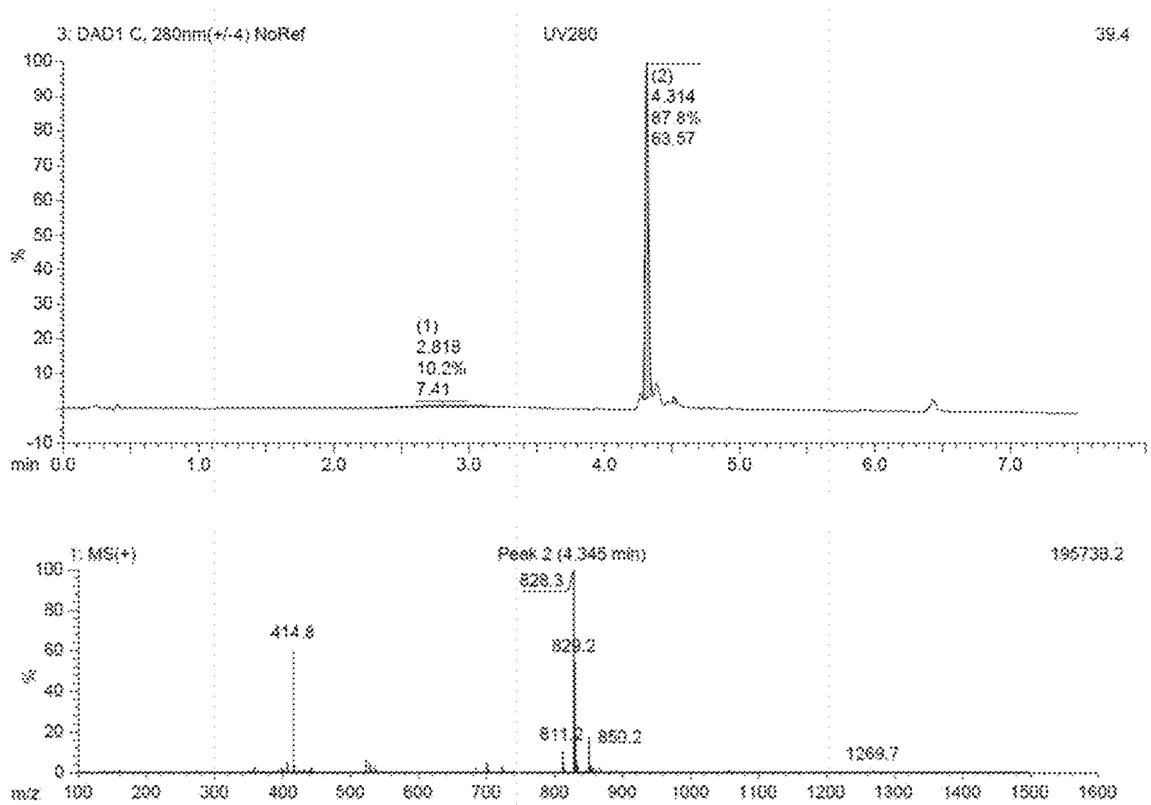

FIGURE 10C

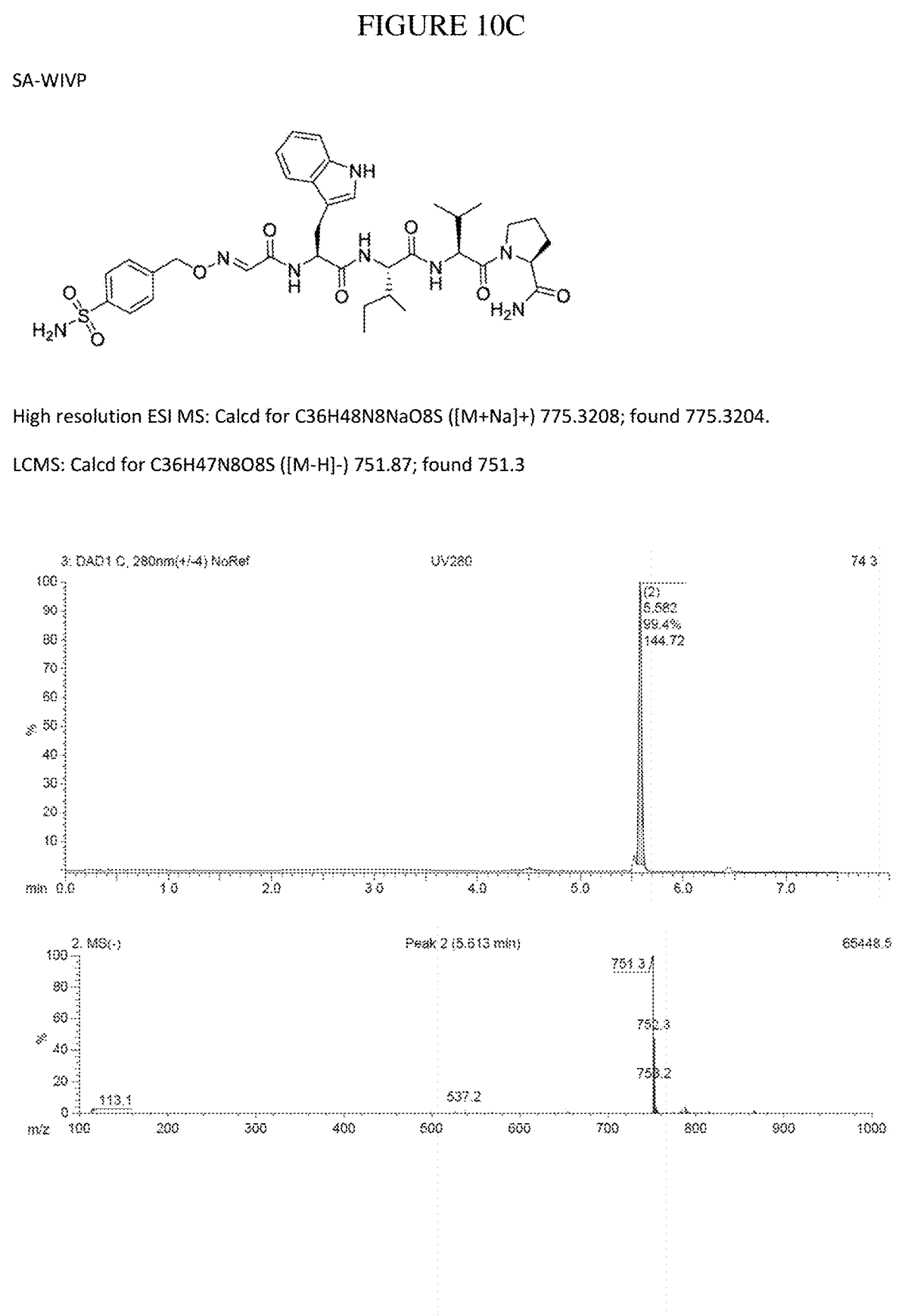

SA-WIVP

High resolution ESI MS: Calcd for C36H48N8NaO8S ([M+Na]+) 775.3208; found 775.3204.

LCMS: Calcd for C36H47N8O8S ([M-H]-) 751.87; found 751.3

3: DAD1 C, 280nm(+/-4) NoRef UV280 74.3

(2) 5.583 99.4% 144.72

2: MS(-) Peak 2 (5.613 min) 65448.5

751.3 752.3 753.2 113.1 537.2

FIGURE 10D
SA-WNTK
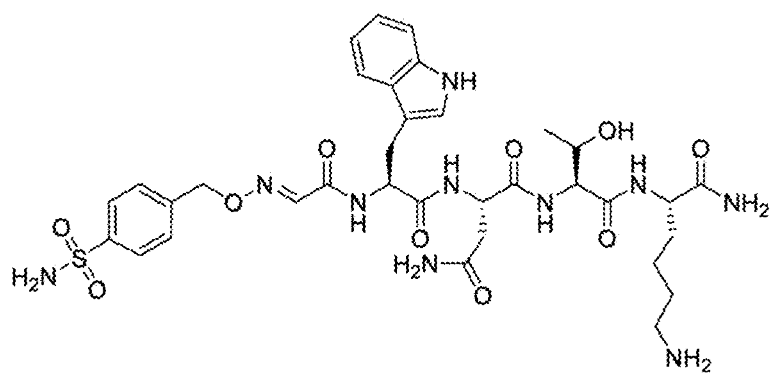
High resolution ESI MS: Calcd for C34H47N10O10S ([M+H]+) 787.3192; found 787.3197.
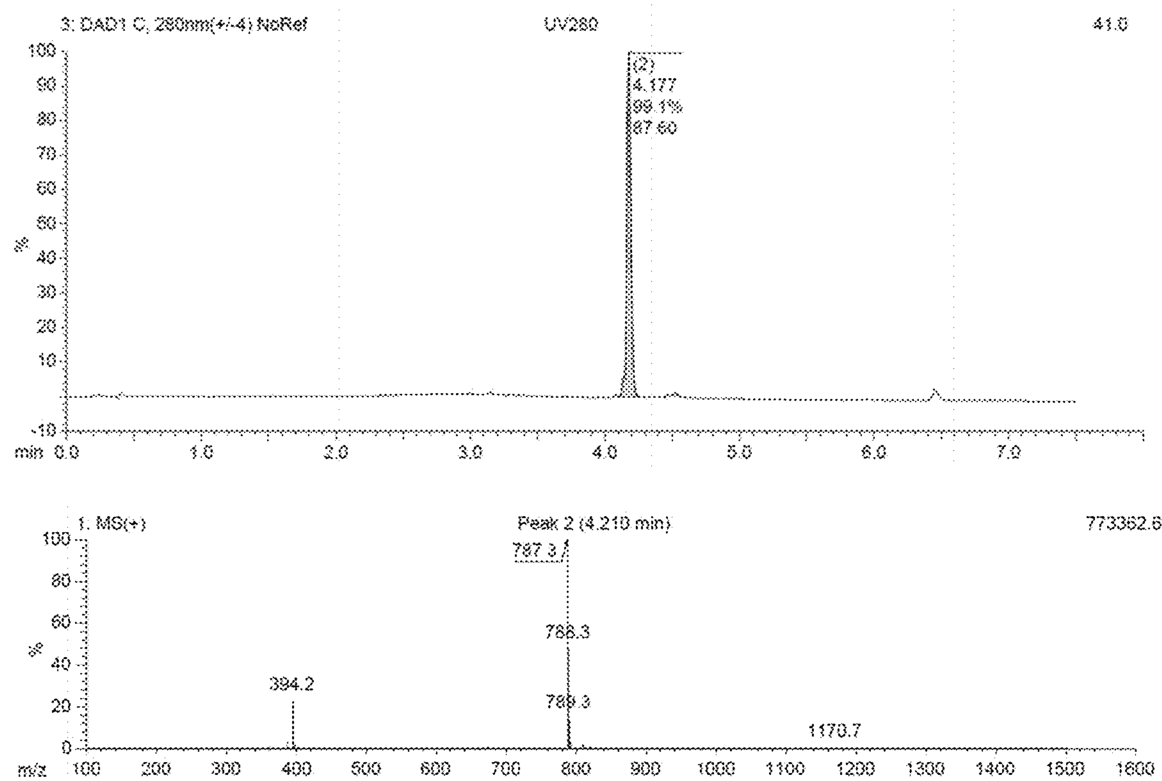

FIGURE 10E
SA-YQYS
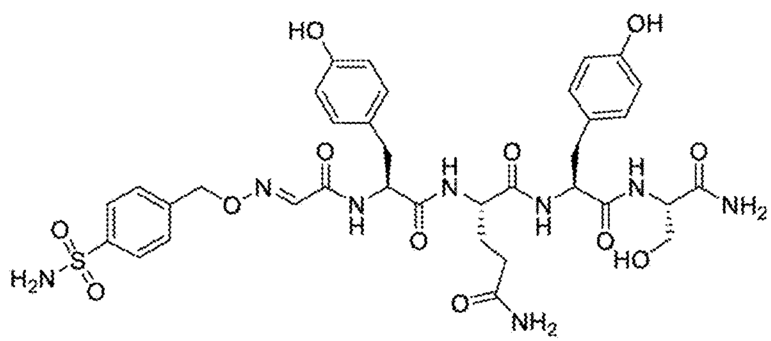
High resolution ESI MS: Calcd for C35H43N8O12S ([M+H]+) 799.2716; found 799.272.
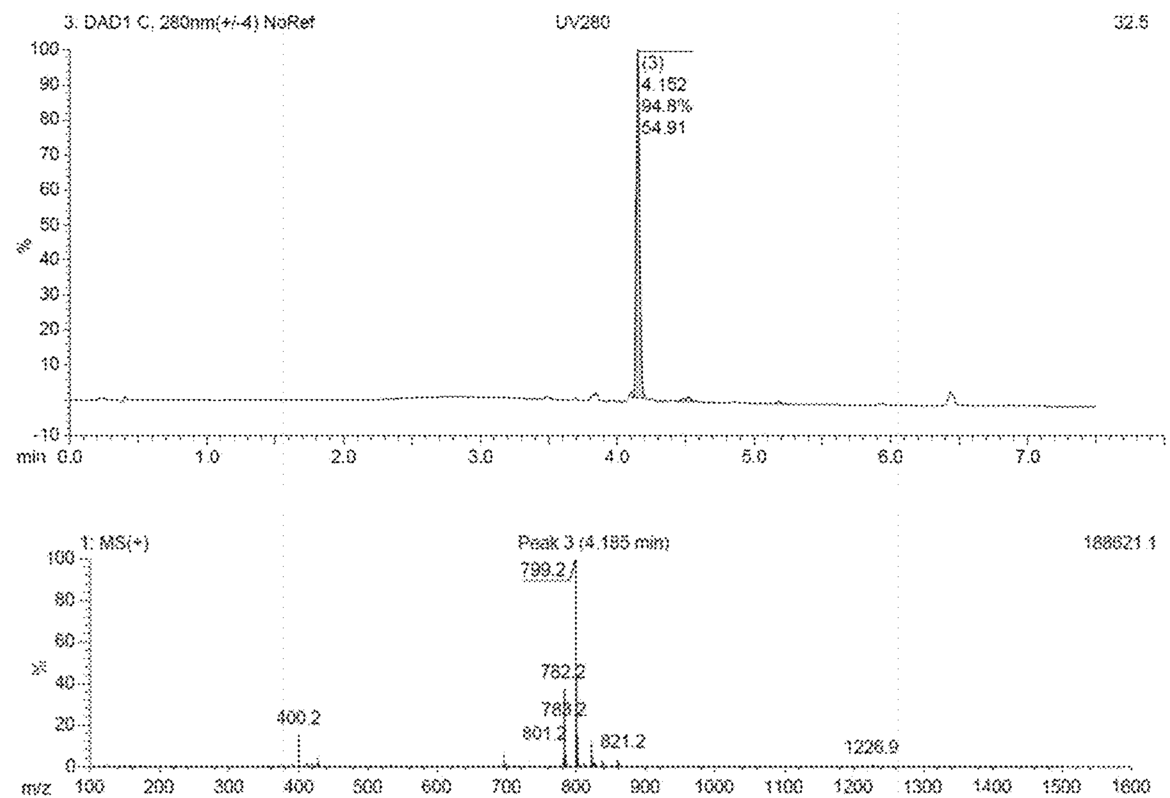

FIGURE 10F
SA-WTSG
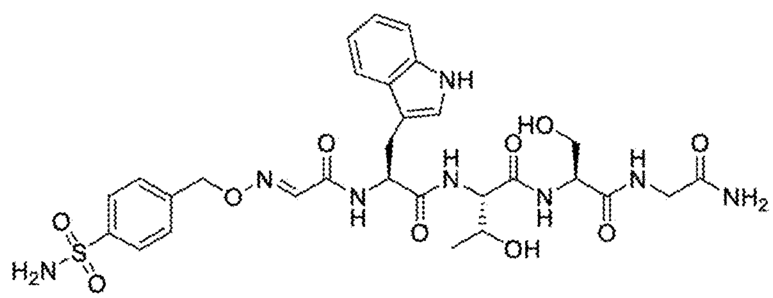
High resolution ESI MS: Calcd for C29H36N8NaO10S ([M+Na]+) 711.2167; found 711.2164.
LCMS: Calcd for C29H35N8O10S ([M-H]-) 687.22; found 687.2.
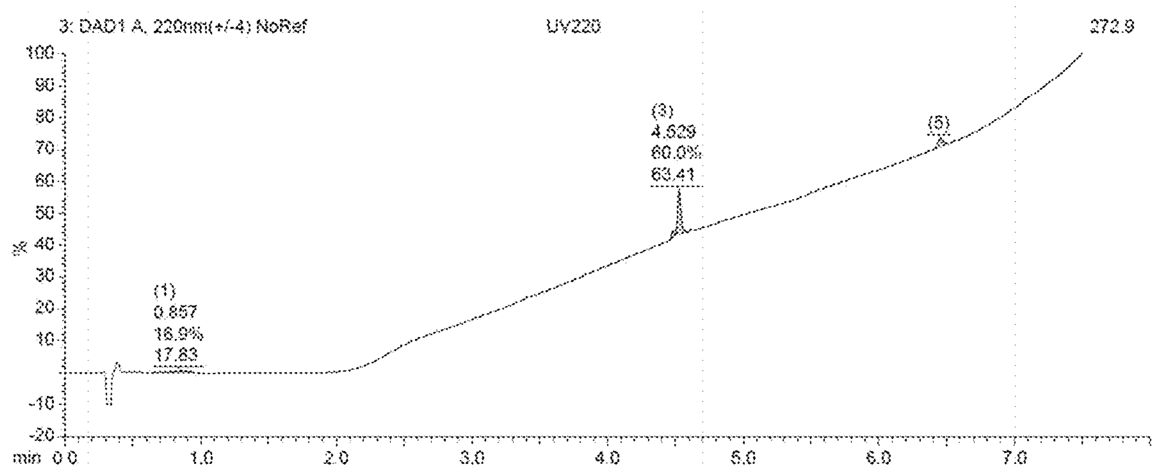
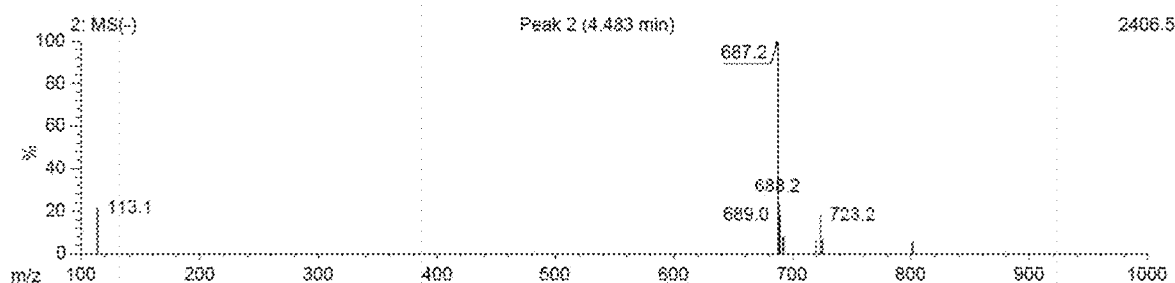

FIGURE 10G
SA-WTWL
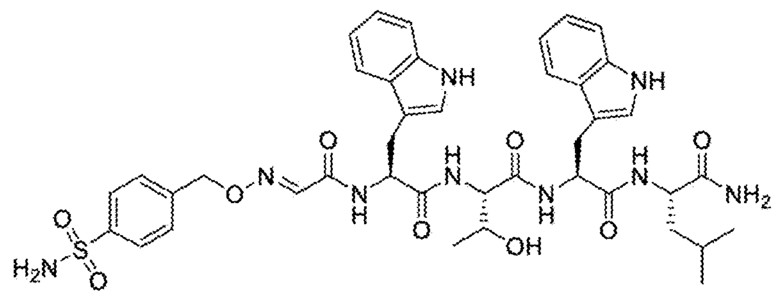
High resolution ESI MS: Calcd for C41H50N9O9S ([M+H]+) 844.3447; found 844.345.
LCMS: Calcd. For C41H50N9O9S ([M-H]-) 843.33; found 842.3.
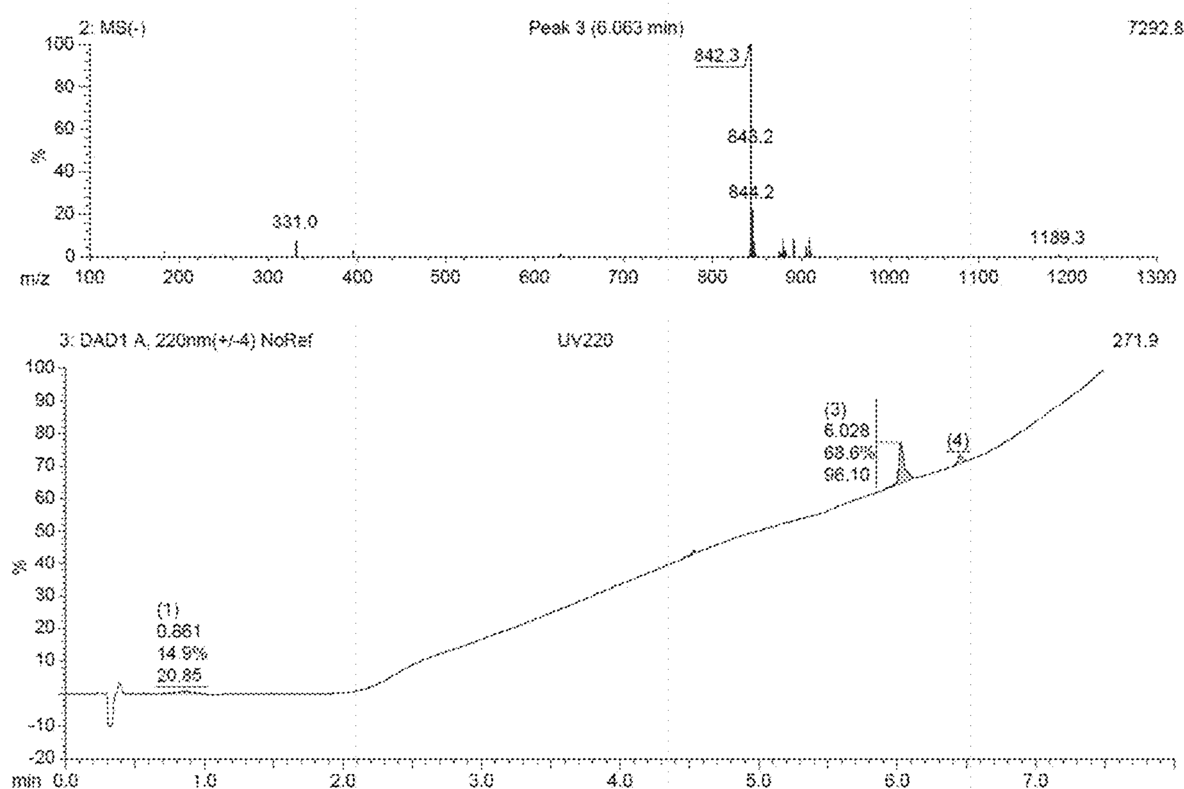

FIGURE 10H
SA-WTYW
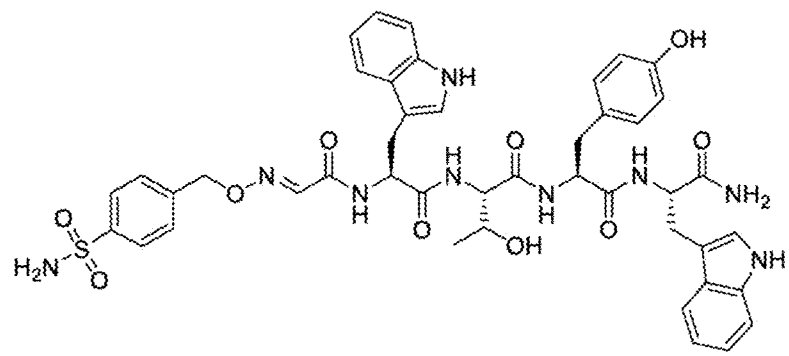
High resolution ESI MS: Calcd for C44H47N9NaO10S ([M+Na]+) 916.3059; found 916.305.
LCMS: Calcd for C44H46N9O10S ([M-H]-): 892.31; found : 892.2
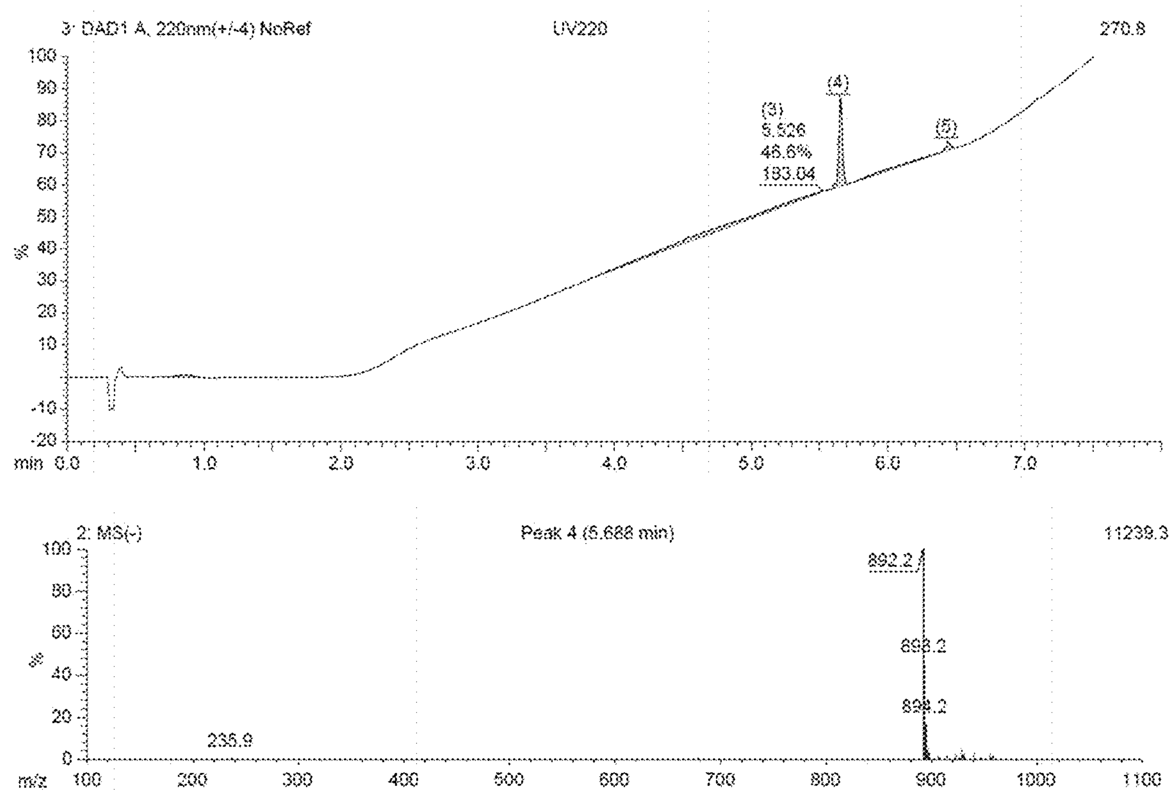

FIGURE 10I
SA-FVVR
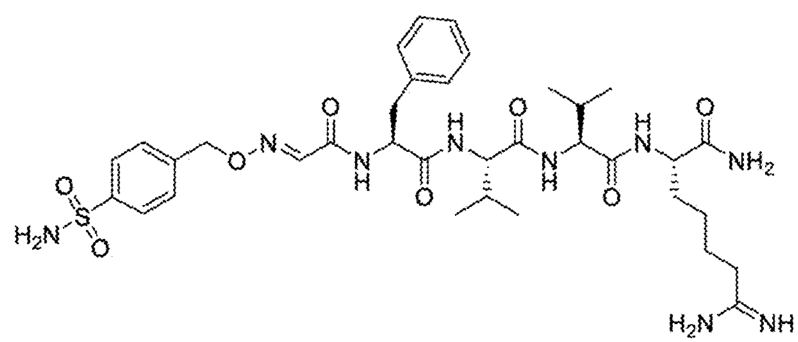
High resolution ESI MS: Calcd for C34H51N10O8S ([M+H]+) 759.3607; found 759.3601
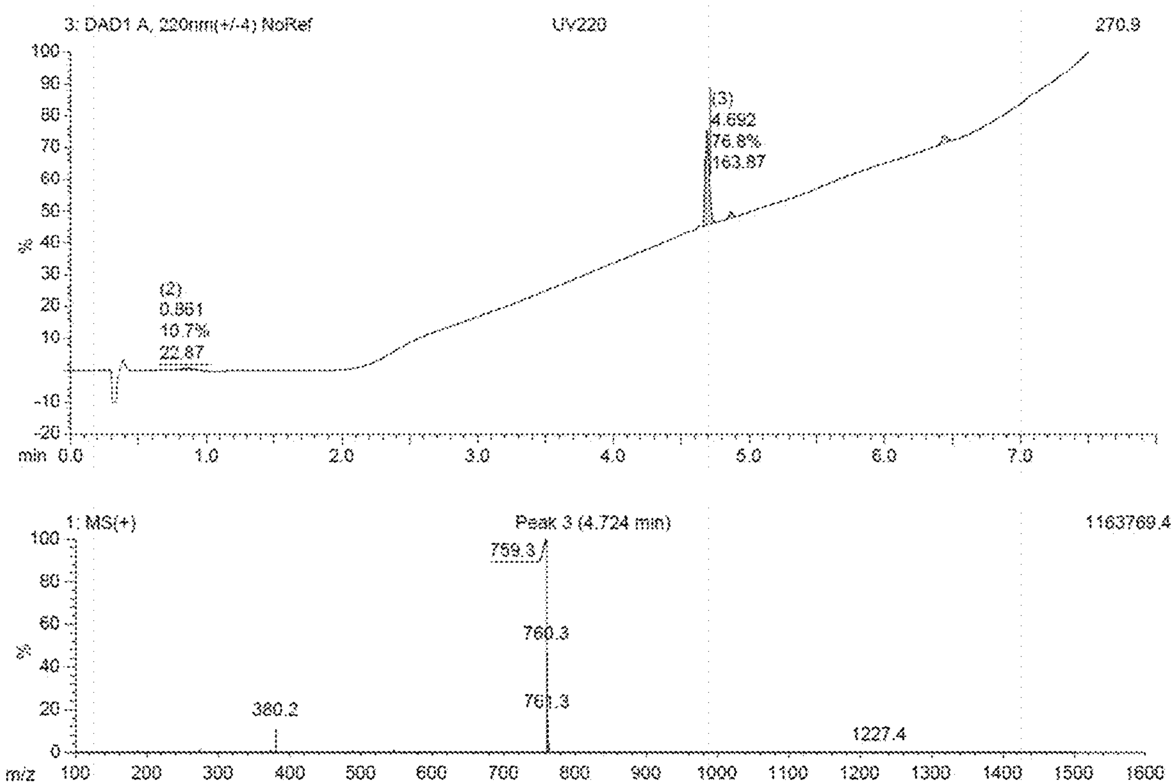

FIGURE 10J
SA-TRPA
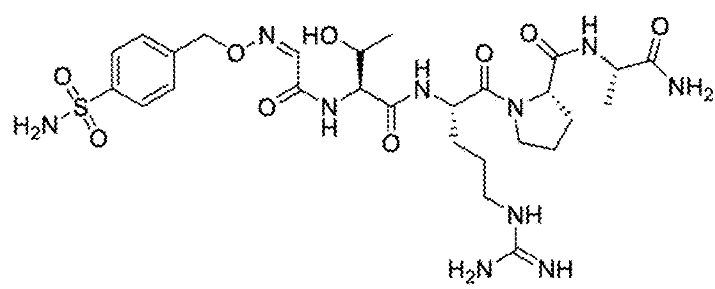
High resolution ESI MS: Calcd for C27H43N10O9S ([M+H]+) 683.293; found 683.2928.
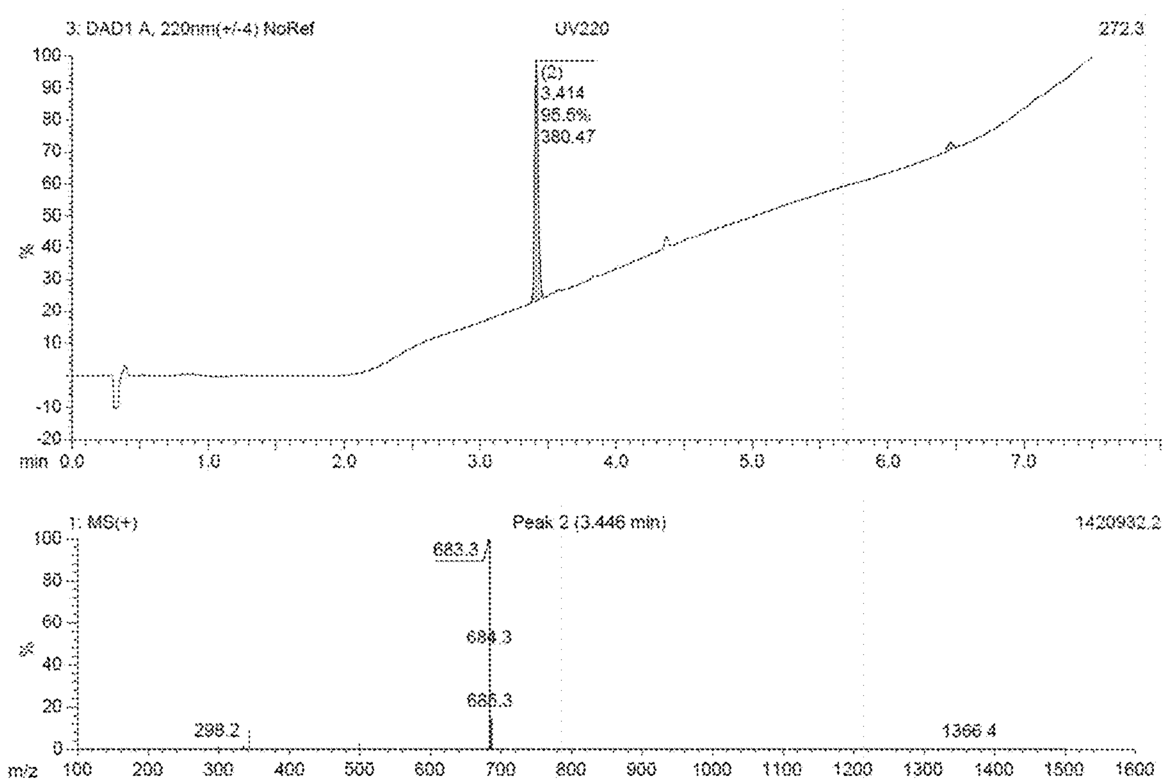

FIGURE 10K
SA-WPAR
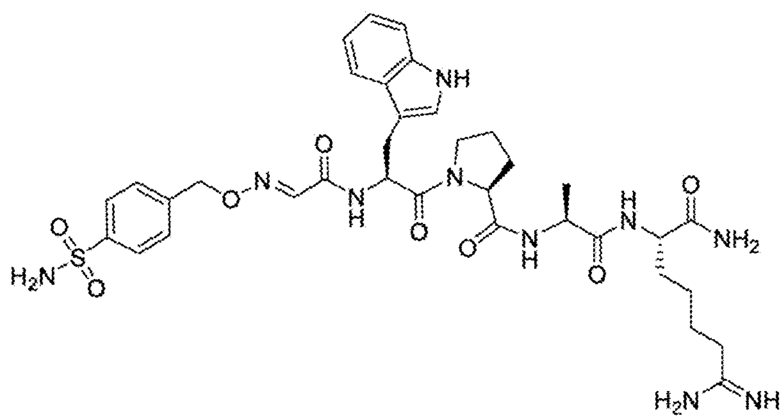
High resolution ESI MS: Calcd for C34H46N11O8S ([M+H]+) 768.3246; found 768.3243.
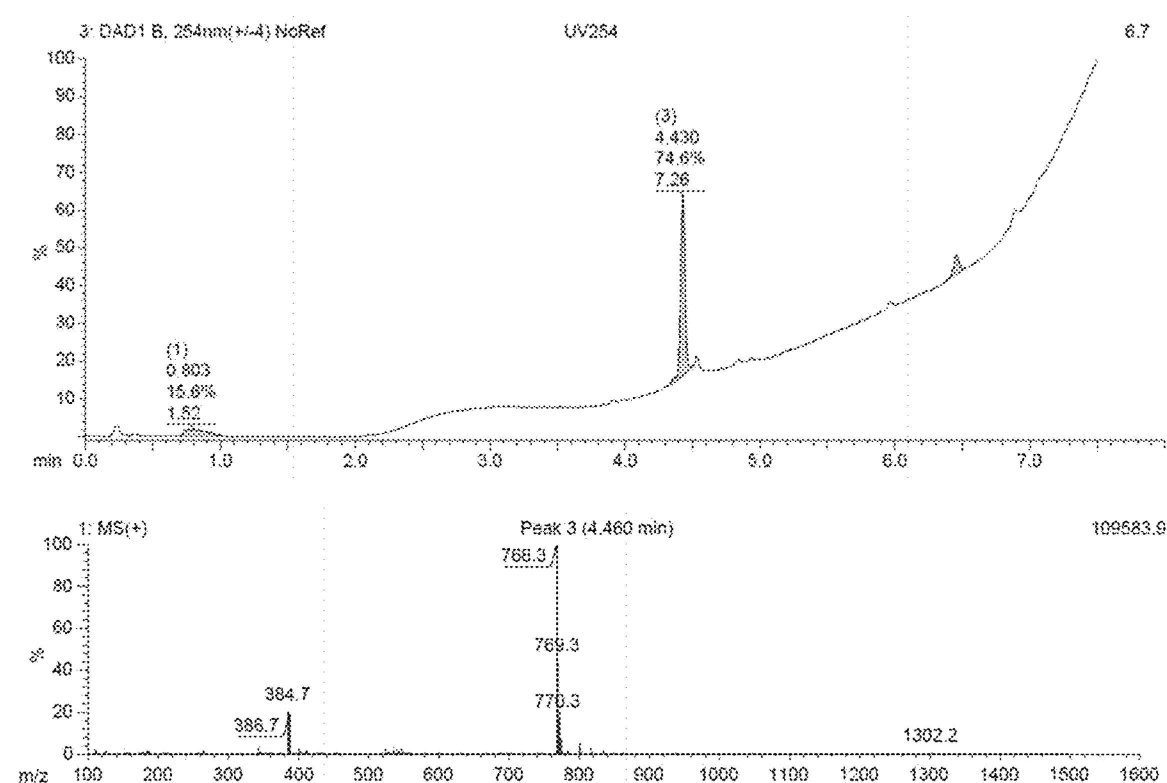

FIGURE 10L
SA-YQYR
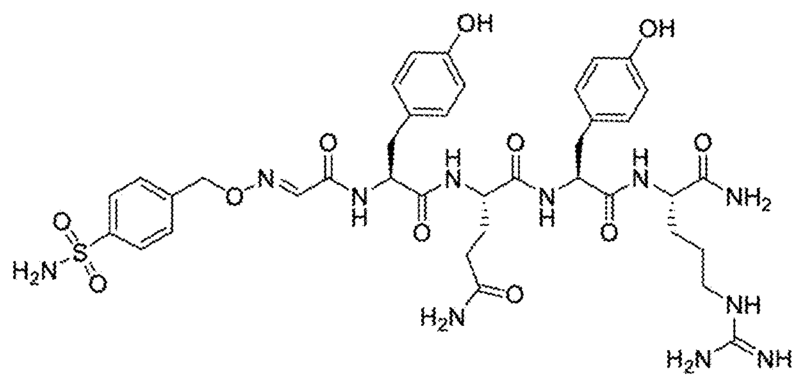
High resolution ESI MS: Calcd for C38 H50 N11 O11 S ([M+H]+) 868.3406; found 868.3402.
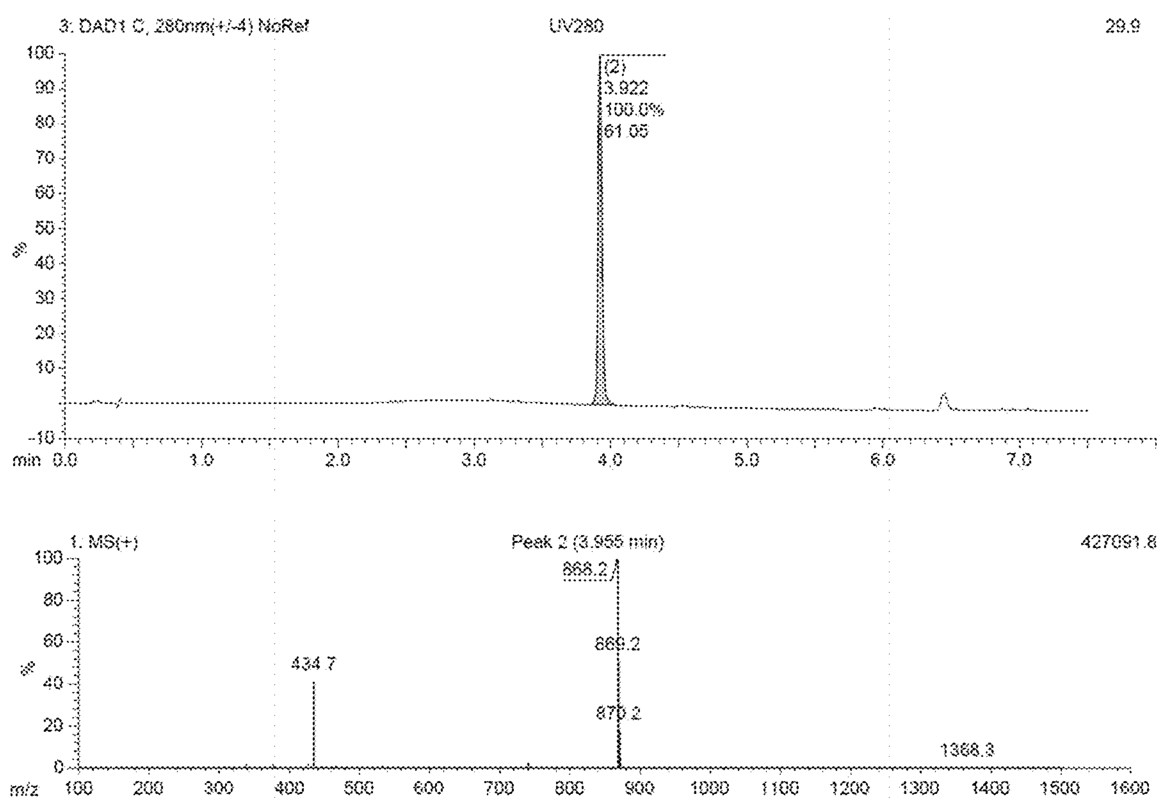

FIGURE 10M
SA-GGGG
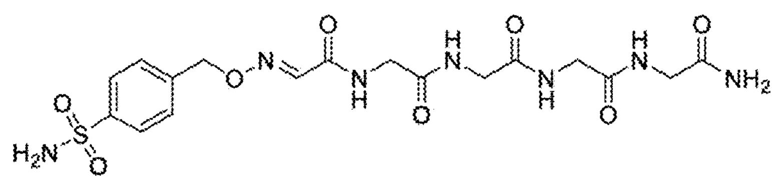
High resolution ESI MS: Calcd for C17H23N7NaO8S ([M+Na]+) 508.1221; found 508.1218.
LCMS: Calcd for C17H22N7O8S ([M-H]-) 484.13; found 484.1
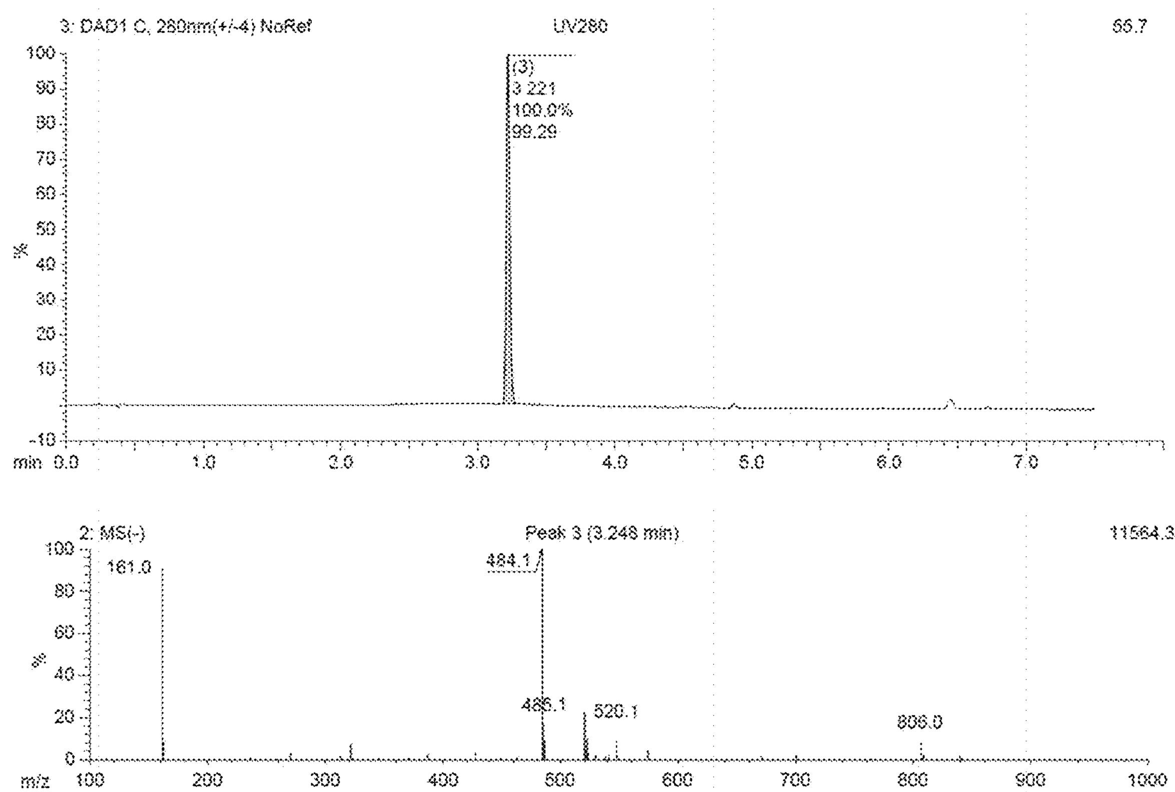

FIGURE 14A
Gal-PAPT
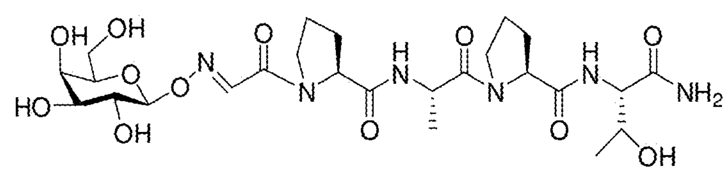
Gal-PAPT
Chemical Formula: $C_{25}H_{40}N_6O_{12}$
Molecular Weight: 616.63
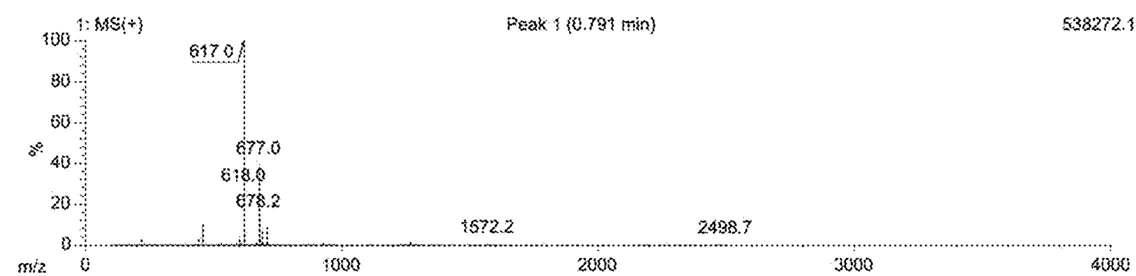
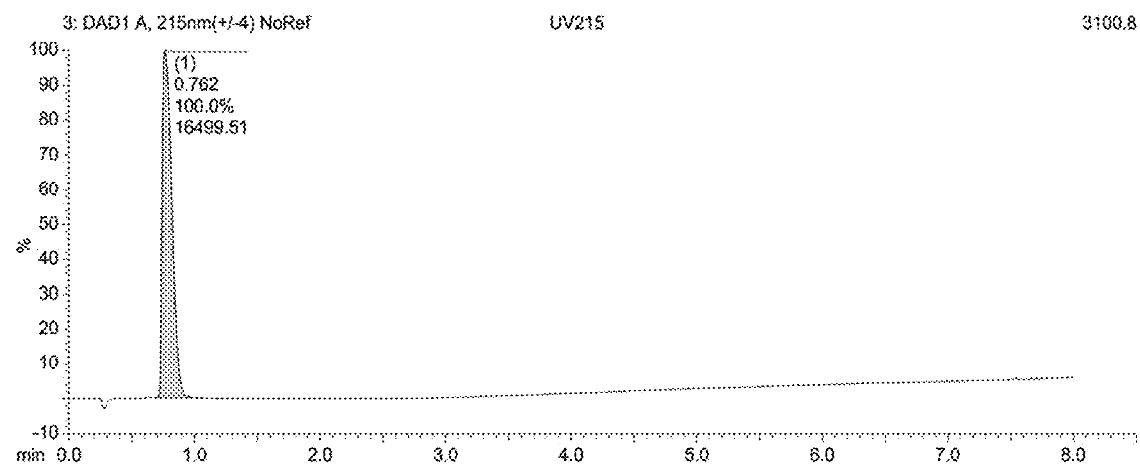

FIGURE 14B
Glu-SIYG
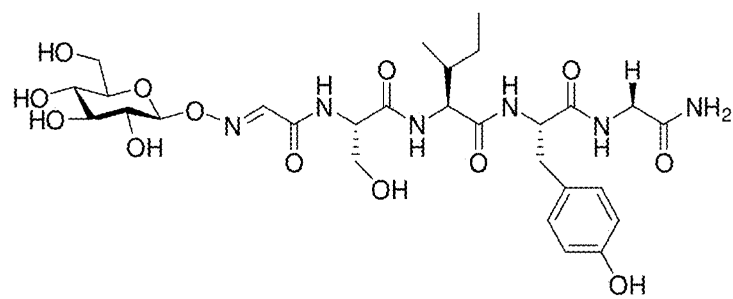
Glu-SIYG
Chemical Formula: $C_{28}H_{42}N_6O_{13}$
Molecular Weight: 670.67
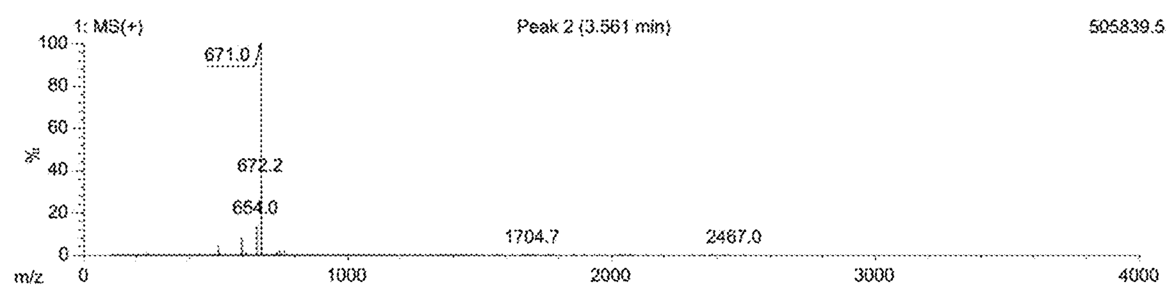
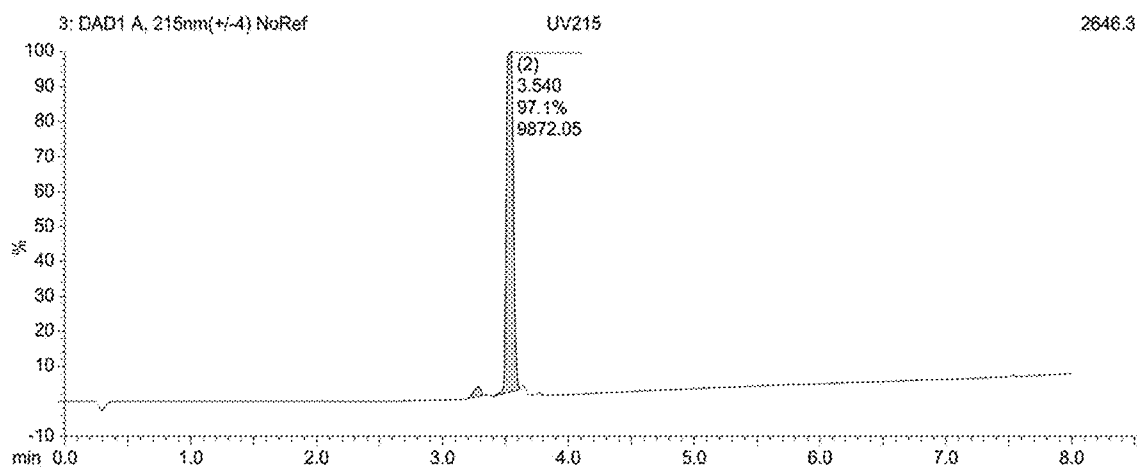

FIGURE 14C

Xyl-ALRV

FIGURE 14D
Rha-IWVR
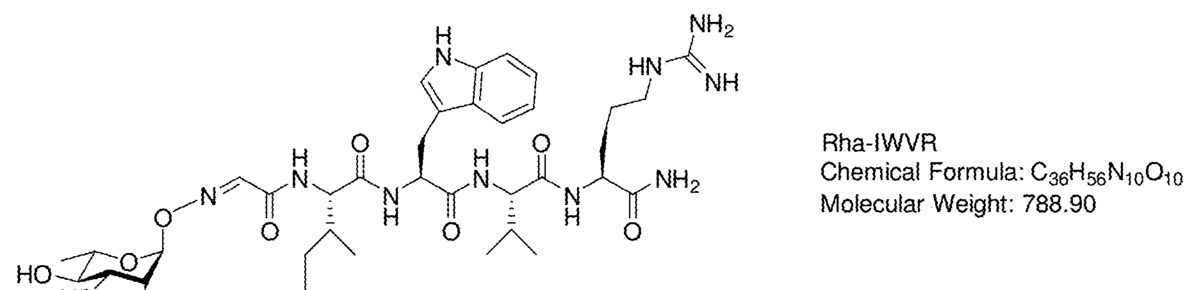
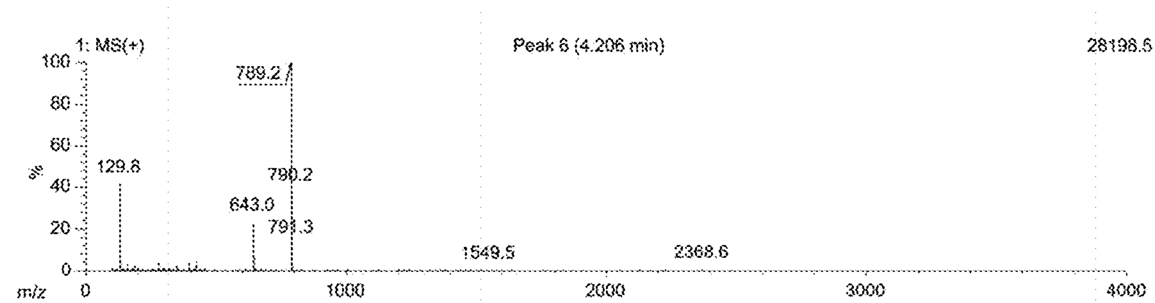
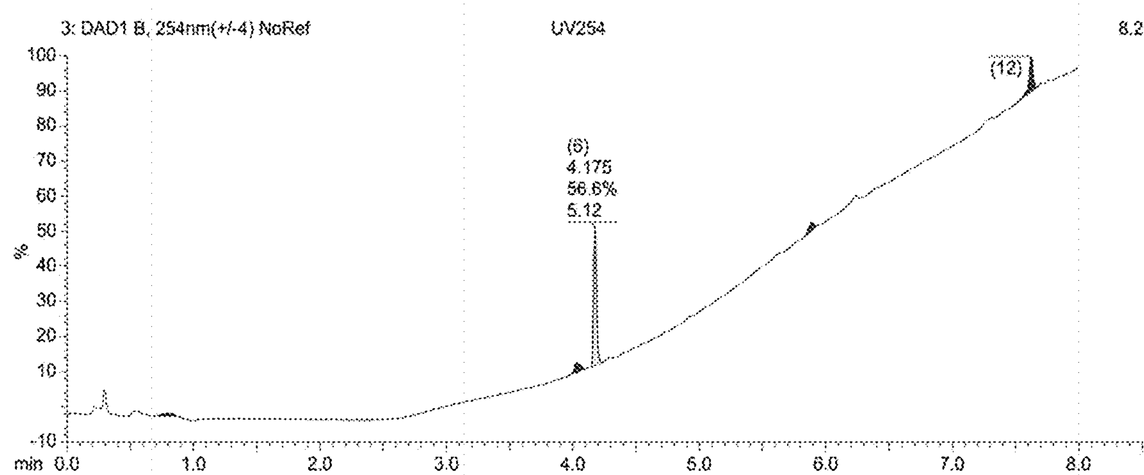

SEQUENCE LISTING

```
<160> NUMBER OF SEQ ID NOS: 115

<210> SEQ ID NO 1
<211> LENGTH: 5
<212> TYPE: PRT
<213> ORGANISM: Artificial Sequence
<220> FEATURE:
<223> OTHER INFORMATION: sulfonamide peptide
<220> FEATURE:
<221> NAME/KEY: MISC_FEATURE
<222> LOCATION: (1)..(1)
<223> OTHER INFORMATION: modified with H2N
<220> FEATURE:
<221> NAME/KEY: MISC_FEATURE
<222> LOCATION: (5)..(5)
<223> OTHER INFORMATION: modified with CONH2

<400> SEQUENCE: 1

Ser Trp Tyr Lys Leu
1               5


<210> SEQ ID NO 2
<211> LENGTH: 4
<212> TYPE: PRT
<213> ORGANISM: Artificial Sequence
<220> FEATURE:
<223> OTHER INFORMATION: sulfonamide peptide product
<220> FEATURE:
<221> NAME/KEY: MISC_FEATURE
<222> LOCATION: (1)..(1)
<223> OTHER INFORMATION: modified with sulfonamide

<400> SEQUENCE: 2

Trp Tyr Lys Leu
1


<210> SEQ ID NO 3
<211> LENGTH: 62
<212> TYPE: DNA
<213> ORGANISM: Artificial Sequence
<220> FEATURE:
<223> OTHER INFORMATION: anti-sense strand from DNA oligonucleotide
      libraries
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

<400> SEQUENCE: 3

gcgcccggcc gaacctccac cmnnmnnmnn mnnagaagag tgagaataga aaggtacccg     60

gg                                                                    62


<210> SEQ ID NO 4
<211> LENGTH: 62
<212> TYPE: DNA
<213> ORGANISM: Artificial Sequence
<220> FEATURE:
<223> OTHER INFORMATION: anti-sense strand of DNA oligonucleotide
      library
```

<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

<400> SEQUENCE: 4
gcgcccggcc gatccacctc cmnnmnnmnn mnnagaagag tgagaataga aaggtacccg 60
gg 62

<210> SEQ ID NO 5
<211> LENGTH: 62
<212> TYPE: DNA
<213> ORGANISM: Artificial Sequence
<220> FEATURE:
<223> OTHER INFORMATION: anti-sense strand of DNA oligonucleotide library
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

<400> SEQUENCE: 5
gcgcccggcc gagccaccgc cmnnmnnmnn mnnagaagag tgagaataga aaggtacccg 60
gg 62

<210> SEQ ID NO 6
<211> LENGTH: 62
<212> TYPE: DNA
<213> ORGANISM: Artificial Sequence
<220> FEATURE:
<223> OTHER INFORMATION: anti-sense strand of oligonucleotide library
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

<400> SEQUENCE: 6

```
gcgcccggcc gatcctcctc cmnnmnnmnn mnnactagag tgagaataga aaggtacccg     60

gg                                                                    62


<210> SEQ ID NO 7
<211> LENGTH: 25
<212> TYPE: DNA
<213> ORGANISM: Artificial Sequence
<220> FEATURE:
<223> OTHER INFORMATION: primer sequence

<400> SEQUENCE: 7

catgcccggg tacctttcta ttctc                                           25


<210> SEQ ID NO 8
<211> LENGTH: 83
<212> TYPE: DNA
<213> ORGANISM: Artificial Sequence
<220> FEATURE:
<223> OTHER INFORMATION: primer for deep-sequencing (forward)
<220> FEATURE:
<221> NAME/KEY: misc_feature
<222> LOCATION: (62)..(65)
<223> OTHER INFORMATION: n is a, c, g, or t

<400> SEQUENCE: 8

caagcagaag acggcatacg agatcggtct cggcattcct gctgaaccgc tcttccgatc     60

tnnnncettt ctattctcac tct                                             83


<210> SEQ ID NO 9
<211> LENGTH: 76
<212> TYPE: DNA
<213> ORGANISM: Artificial Sequence
<220> FEATURE:
<223> OTHER INFORMATION: primer for deep-sequencing (reverse)
<220> FEATURE:
<221> NAME/KEY: misc_feature
<222> LOCATION: (59)..(62)
<223> OTHER INFORMATION: n is a, c, g, or t

<400> SEQUENCE: 9

aatgatacgg cgaccaccga gatctacact ctttccctac acgacgctct tccgatctnn     60

nnacagtttc ggccga                                                     76


<210> SEQ ID NO 10
<211> LENGTH: 8
<212> TYPE: PRT
<213> ORGANISM: Artificial Sequence
<220> FEATURE:
<223> OTHER INFORMATION: peptide linker for libraries with silent
      barcodes
<220> FEATURE:
<221> NAME/KEY: misc_feature
<222> LOCATION: (2)..(5)
<223> OTHER INFORMATION: Xaa can be any naturally occurring amino acid

<400> SEQUENCE: 10

Ser Xaa Xaa Xaa Xaa Gly Gly Gly
1               5


<210> SEQ ID NO 11
<211> LENGTH: 24
<212> TYPE: DNA
<213> ORGANISM: Artificial Sequence
<220> FEATURE:
<223> OTHER INFORMATION: silent barcode (HB1)
<220> FEATURE:
```

```
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t

<400> SEQUENCE: 11

tctnnknnkn nknnkggtgg aggt                                            24


<210> SEQ ID NO 12
<211> LENGTH: 24
<212> TYPE: DNA
<213> ORGANISM: Artificial Sequence
<220> FEATURE:
<223> OTHER INFORMATION: silent barcode (HB2)
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t

<400> SEQUENCE: 12

tctnnknnkn nknnkggagg tgga                                            24


<210> SEQ ID NO 13
<211> LENGTH: 24
<212> TYPE: DNA
<213> ORGANISM: Artificial Sequence
<220> FEATURE:
<223> OTHER INFORMATION: silent barcode (HB3)
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t

<400> SEQUENCE: 13

tctnnknnkn nknnkggcgg tggc                                            24


<210> SEQ ID NO 14
<211> LENGTH: 24
```

<212> TYPE: DNA
<213> ORGANISM: Artificial Sequence
<220> FEATURE:
<223> OTHER INFORMATION: silent barcode (HB4)
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t

<400> SEQUENCE: 14
agtnnknnkn nknnkggtgg tggt 24

<210> SEQ ID NO 15
<211> LENGTH: 24
<212> TYPE: DNA
<213> ORGANISM: Artificial Sequence
<220> FEATURE:
<223> OTHER INFORMATION: silent barcode (HB5)
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t

<400> SEQUENCE: 15
agtnnknnkn nknnkggcgg cggc 24

<210> SEQ ID NO 16
<211> LENGTH: 24
<212> TYPE: DNA
<213> ORGANISM: Artificial Sequence
<220> FEATURE:
<223> OTHER INFORMATION: silent barcode (HB6)
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t

<400> SEQUENCE: 16
agtnnknnkn nknnkggagg agga 24

<210> SEQ ID NO 17
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 17

His Pro Pro Arg
1

<210> SEQ ID NO 18
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 18

Gly Tyr Thr Gln
1

<210> SEQ ID NO 19
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 19

Pro Leu His Pro
1

<210> SEQ ID NO 20
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 20

His Pro Ser Tyr
1

<210> SEQ ID NO 21
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 21

Pro Gln Met Ser
1

<210> SEQ ID NO 22
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 22

Ala His Pro Leu
1

<210> SEQ ID NO 23
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 23

Trp Asn Ser Lys
1

<210> SEQ ID NO 24
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 24

Trp Thr Tyr Val
1

<210> SEQ ID NO 25
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 25

Trp Asn Thr Lys
1

<210> SEQ ID NO 26
<211> LENGTH: 4

<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 26

Trp Ile Val Pro
1

<210> SEQ ID NO 27
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 27

Trp Gln Gln Gln
1

<210> SEQ ID NO 28
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 28

Tyr Gln Tyr Ser
1

<210> SEQ ID NO 29
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 29

Tyr Gly Thr His
1

<210> SEQ ID NO 30
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 30

Thr Ala Phe Ile
1

<210> SEQ ID NO 31
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 31

Trp Thr Ser Gly
1

<210> SEQ ID NO 32
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 32

Tyr Met Ser Asn
1

<210> SEQ ID NO 33
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 33

Trp Thr Trp Leu
1

<210> SEQ ID NO 34
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 34

Trp Thr Tyr Trp
1

<210> SEQ ID NO 35
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:

<221> NAME/KEY: MISC_FEATURE
<222> LOCATION: (1)..(1)
<223> OTHER INFORMATION: modified with sulfonamide

<400> SEQUENCE: 35

Trp Pro Pro Tyr
1

<210> SEQ ID NO 36
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 36

Trp Pro Pro Pro
1

<210> SEQ ID NO 37
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 37

Trp Asp Met Asp
1

<210> SEQ ID NO 38
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 38

Trp Phe Glu Asn
1

<210> SEQ ID NO 39
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 39

Trp Pro Ala Arg
1

<210> SEQ ID NO 40

<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 40

Trp Leu Val Leu
1

<210> SEQ ID NO 41
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 41

Trp Phe Lys Leu
1

<210> SEQ ID NO 42
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 42

Trp Lys Gln Gln
1

<210> SEQ ID NO 43
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 43

Trp Ser Val Met
1

<210> SEQ ID NO 44
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modifed with sulfonamide

<400> SEQUENCE: 44

Gln Ile Glu His
1

<210> SEQ ID NO 45
<211> LENGTH: 24
<212> TYPE: DNA
<213> ORGANISM: Artificial Sequence
<220> FEATURE:
<223> OTHER INFORMATION: sequence identified in panning a mixed-
modification library (using carbonic anhydrase)

<400> SEQUENCE: 45
agttggtata agttgggagg agga 24

<210> SEQ ID NO 46
<211> LENGTH: 24
<212> TYPE: DNA
<213> ORGANISM: Artificial Sequence
<220> FEATURE:
<223> OTHER INFORMATION: sequence identified in panning of a mixed-
modification library (using carbonic anhydrase)

<400> SEQUENCE: 46
agttggcagc agcagggagg agga 24

<210> SEQ ID NO 47
<211> LENGTH: 24
<212> TYPE: DNA
<213> ORGANISM: Artificial Sequence
<220> FEATURE:
<223> OTHER INFORMATION: sequence identified in panning of a mixed-
modification library (using carbonic anhydrase)

<400> SEQUENCE: 47
agttggattg ttcctggagg agga 24

<210> SEQ ID NO 48
<211> LENGTH: 24
<212> TYPE: DNA
<213> ORGANISM: Artificial Sequence
<220> FEATURE:
<223> OTHER INFORMATION: sequence identified in panning of a mixed-
modification library (using carbonic anhydrase)

<400> SEQUENCE: 48
agttggaata cgaagggagg agga 24

<210> SEQ ID NO 49
<211> LENGTH: 24
<212> TYPE: DNA
<213> ORGANISM: Artificial Sequence
<220> FEATURE:
<223> OTHER INFORMATION: sequence identified in panning of a mixed-
modification library (using carbonic anhydrase)

<400> SEQUENCE: 49
agttatcagt atagtggagg agga 24

<210> SEQ ID NO 50
<211> LENGTH: 24
<212> TYPE: DNA
<213> ORGANISM: Artificial Sequence
<220> FEATURE:
<223> OTHER INFORMATION: sequence identified in panning of a mixed-
modification library (using carbonic anhydrase)

<400> SEQUENCE: 50
agttatggta cgcatggagg agga 24

<210> SEQ ID NO 51
<211> LENGTH: 24
<212> TYPE: DNA
<213> ORGANISM: Artificial Sequence
<220> FEATURE:
<223> OTHER INFORMATION: sequence identified in panning of a mixed-
modification library (using carbonic anhydrase)

<400> SEQUENCE: 51
agtacggcgt ttattggagg agga 24

<210> SEQ ID NO 52
<211> LENGTH: 24
<212> TYPE: DNA
<213> ORGANISM: Artificial Sequence
<220> FEATURE:
<223> OTHER INFORMATION: sequence identified in panning of a mixed-
modification library (using carbonic anhydrase)

<400> SEQUENCE: 52
agttggactt ctgggggagg agga 24

<210> SEQ ID NO 53
<211> LENGTH: 24
<212> TYPE: DNA
<213> ORGANISM: Artificial Sequence
<220> FEATURE:
<223> OTHER INFORMATION: sequence identified in panning of a mixed-
modification library (using carbonic anhydrase)

<400> SEQUENCE: 53
agttatatgt ctaatggagg agga 24

<210> SEQ ID NO 54
<211> LENGTH: 24
<212> TYPE: DNA
<213> ORGANISM: Artificial Sequence
<220> FEATURE:
<223> OTHER INFORMATION: sequence identified in panning of a mixed-
modification library (using carbonic anhydrase)

<400> SEQUENCE: 54
agttggactt ggttgggagg agga 24

<210> SEQ ID NO 55
<211> LENGTH: 24
<212> TYPE: DNA
<213> ORGANISM: Artificial Sequence
<220> FEATURE:
<223> OTHER INFORMATION: sequence identified in panning of a mixed-
modification library (using carbonic anhydrase)

<400> SEQUENCE: 55
agtcagattg agcatggagg agga 24

<210> SEQ ID NO 56
<211> LENGTH: 24
<212> TYPE: DNA
<213> ORGANISM: Artificial Sequence
<220> FEATURE:
<223> OTHER INFORMATION: sequence identified in panning of a mixed-
modification library (using carbonic anhydrase)

<400> SEQUENCE: 56
agttggacgt attggggagg agga 24

<210> SEQ ID NO 57
<211> LENGTH: 24
<212> TYPE: DNA
<213> ORGANISM: Artificial Sequence
<220> FEATURE:
<223> OTHER INFORMATION: sequence identified in panning of a mixed-modification library (using carbonic anhydrase)

<400> SEQUENCE: 57
agttggccgc cttatggagg agga 24

<210> SEQ ID NO 58
<211> LENGTH: 24
<212> TYPE: DNA
<213> ORGANISM: Artificial Sequence
<220> FEATURE:
<223> OTHER INFORMATION: sequence identified in panning of a mixed-modification library (using carbonic anhydrase)

<400> SEQUENCE: 58
agttggccgc ctccgggagg agga 24

<210> SEQ ID NO 59
<211> LENGTH: 24
<212> TYPE: DNA
<213> ORGANISM: Artificial Sequence
<220> FEATURE:
<223> OTHER INFORMATION: sequence identified in panning of a mixed-modification library (using carbonic anhydrase)

<400> SEQUENCE: 59
agttggattg ttccaggagg agga 24

<210> SEQ ID NO 60
<211> LENGTH: 24
<212> TYPE: DNA
<213> ORGANISM: Artificial Sequence
<220> FEATURE:
<223> OTHER INFORMATION: sequence identified in panning of a mixed-modification library (using carbonic anhydrase)

<400> SEQUENCE: 60
agttggctgg tgcttggagg agga 24

<210> SEQ ID NO 61
<211> LENGTH: 24
<212> TYPE: DNA
<213> ORGANISM: Artificial Sequence
<220> FEATURE:
<223> OTHER INFORMATION: sequence identified in panning of a mixed-modification library (using carbonic anhydrase)

<400> SEQUENCE: 61
agttggttta agttgggagg agga 24

<210> SEQ ID NO 62
<211> LENGTH: 24
<212> TYPE: DNA
<213> ORGANISM: Artificial Sequence
<220> FEATURE:
<223> OTHER INFORMATION: sequence identified in panning of a mixed-modification library (using carbonic anhydrase)

<400> SEQUENCE: 62
agttggaagc agcagggagg agga 24

<210> SEQ ID NO 63
<211> LENGTH: 24
<212> TYPE: DNA
<213> ORGANISM: Artificial Sequence
<220> FEATURE:
<223> OTHER INFORMATION: sequence identified in panning of a mixed-modification library (using carbonic anhydrase)

<400> SEQUENCE: 63
agttggagtg ttatgggagg agga 24

<210> SEQ ID NO 64
<211> LENGTH: 24
<212> TYPE: DNA
<213> ORGANISM: Artificial Sequence
<220> FEATURE:
<223> OTHER INFORMATION: sequence identified in panning of a mixed-modification library (using carbonic anhydrase)

<400> SEQUENCE: 64
agttggaatt cgaagggagg agga 24

<210> SEQ ID NO 65
<211> LENGTH: 24
<212> TYPE: DNA
<213> ORGANISM: Artificial Sequence
<220> FEATURE:
<223> OTHER INFORMATION: sequence identified in panning of a mixed-modification library (using streptavidin)

<400> SEQUENCE: 65
tctccgcaga tgtctggcgg tggc 24

<210> SEQ ID NO 66
<211> LENGTH: 24
<212> TYPE: DNA
<213> ORGANISM: Artificial Sequence
<220> FEATURE:
<223> OTHER INFORMATION: sequence identified in panning of a mixed-modification library (using streptavidin)

<400> SEQUENCE: 66
tctgcgcatc ctttgggcgg tggc 24

<210> SEQ ID NO 67
<211> LENGTH: 24
<212> TYPE: DNA
<213> ORGANISM: Artificial Sequence
<220> FEATURE:
<223> OTHER INFORMATION: sequence identified in panning of a mixed-modification library (using streptavidin)

<400> SEQUENCE: 67
tctggttata cgcagggcgg tggc 24

<210> SEQ ID NO 68
<211> LENGTH: 24
<212> TYPE: DNA
<213> ORGANISM: Artificial Sequence
<220> FEATURE:
<223> OTHER INFORMATION: sequence identified in panning of a mixed-modification library (using streptavidin)

<400> SEQUENCE: 68
tctcatttta cgaatggcgg tggc 24

<210> SEQ ID NO 69
<211> LENGTH: 24
<212> TYPE: DNA
<213> ORGANISM: Artificial Sequence
<220> FEATURE:
<223> OTHER INFORMATION: sequence identified in panning of a mixed-modification library (using streptavidin)

<400> SEQUENCE: 69
tctcctactc atactggcgg tggc 24

<210> SEQ ID NO 70
<211> LENGTH: 24
<212> TYPE: DNA
<213> ORGANISM: Artificial Sequence
<220> FEATURE:
<223> OTHER INFORMATION: sequence identified in panning of a mixed-modification library (using streptavidin)

<400> SEQUENCE: 70
tctccgtcga ttggtggcgg tggc 24

<210> SEQ ID NO 71
<211> LENGTH: 24
<212> TYPE: DNA
<213> ORGANISM: Artificial Sequence
<220> FEATURE:
<223> OTHER INFORMATION: sequence identified in panning of a mixed-modification library (using streptavidin)

<400> SEQUENCE: 71
tctccggcgc ttcctggcgg tggc 24

<210> SEQ ID NO 72
<211> LENGTH: 24
<212> TYPE: DNA
<213> ORGANISM: Artificial Sequence
<220> FEATURE:
<223> OTHER INFORMATION: sequence identified in panning of a mixed-modification library (using streptavidin)

<400> SEQUENCE: 72
tctcatccga gttatggcgg tggc 24

<210> SEQ ID NO 73
<211> LENGTH: 24
<212> TYPE: DNA
<213> ORGANISM: Artificial Sequence
<220> FEATURE:
<223> OTHER INFORMATION: sequence identified in panning of a mixed-modification library (using streptavidin)

<400> SEQUENCE: 73
tcttggtatc ctcatggcgg tggc 24

<210> SEQ ID NO 74
<211> LENGTH: 24
<212> TYPE: DNA
<213> ORGANISM: Artificial Sequence
<220> FEATURE:
<223> OTHER INFORMATION: sequence identified in panning of a mixed-modification library (using streptavidin)

<400> SEQUENCE: 74
tctcatttga gggttggcgg tggc 24

<210> SEQ ID NO 75
<211> LENGTH: 24
<212> TYPE: DNA
<213> ORGANISM: Artificial Sequence
<220> FEATURE:
<223> OTHER INFORMATION: sequence identified in panning of a mixed-
modification library (using streptavidin)

<400> SEQUENCE: 75
tctcatatgc cgcgtggcgg tggc 24

<210> SEQ ID NO 76
<211> LENGTH: 24
<212> TYPE: DNA
<213> ORGANISM: Artificial Sequence
<220> FEATURE:
<223> OTHER INFORMATION: sequence identified in panning of a mixed-
modification library (using streptavidin)

<400> SEQUENCE: 76
tctcctgttt cgattggcgg tggc 24

<210> SEQ ID NO 77
<211> LENGTH: 24
<212> TYPE: DNA
<213> ORGANISM: Artificial Sequence
<220> FEATURE:
<223> OTHER INFORMATION: sequence identified in panning of a mixed-
modification library (using streptavidin)

<400> SEQUENCE: 77
tcttatatga ataatggcgg tggc 24

<210> SEQ ID NO 78
<211> LENGTH: 24
<212> TYPE: DNA
<213> ORGANISM: Artificial Sequence
<220> FEATURE:
<223> OTHER INFORMATION: sequence identified in panning of a mixed-
modification library (using streptavidin)

<400> SEQUENCE: 78
tctcataagc tgaatggcgg tggc 24

<210> SEQ ID NO 79
<211> LENGTH: 24
<212> TYPE: DNA
<213> ORGANISM: Artificial Sequence
<220> FEATURE:
<223> OTHER INFORMATION: sequence identified in panning of a mixed-
modification library (using streptavidin)

<400> SEQUENCE: 79
tctcctcatc tgcctggcgg tggc 24

<210> SEQ ID NO 80
<211> LENGTH: 24
<212> TYPE: DNA
<213> ORGANISM: Artificial Sequence
<220> FEATURE:
<223> OTHER INFORMATION: sequence identified in panning of a mixed-
modification library (using streptavidin)

<400> SEQUENCE: 80
tctcctcatt ataatggcgg tggc 24

<210> SEQ ID NO 81

<211> LENGTH: 24
<212> TYPE: DNA
<213> ORGANISM: Artificial Sequence
<220> FEATURE:
<223> OTHER INFORMATION: sequence identified in panning of a mixed-
modification library (using streptavidin)

<400> SEQUENCE: 81
tctcctctgg cgcagggcgg tggc 24

<210> SEQ ID NO 82
<211> LENGTH: 24
<212> TYPE: DNA
<213> ORGANISM: Artificial Sequence
<220> FEATURE:
<223> OTHER INFORMATION: sequence identified in panning of a mixed-
modification library (using streptavidin)

<400> SEQUENCE: 82
tctgtgcatg cgtggggcgg tggc 24

<210> SEQ ID NO 83
<211> LENGTH: 24
<212> TYPE: DNA
<213> ORGANISM: Artificial Sequence
<220> FEATURE:
<223> OTHER INFORMATION: sequence identified in panning of a mixed-
modification library (using streptavidin)

<400> SEQUENCE: 83
tctgtgcata atactggcgg tggc 24

<210> SEQ ID NO 84
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 84

His Phe Thr Asn
1

<210> SEQ ID NO 85
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 85

Pro Thr His Thr
1

<210> SEQ ID NO 86
<211> LENGTH: 4
<212> TYPE: PRT
<213> ORGANISM: Artificial Sequence
<220> FEATURE:
<223> OTHER INFORMATION: biotin-modified peptide
<220> FEATURE:

<221> NAME/KEY: MISC_FEATURE
<222> LOCATION: (1)..(1)
<223> OTHER INFORMATION: modified with biotin

<400> SEQUENCE: 86

Pro Ser Ile Gly
1

<210> SEQ ID NO 87
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 87

Pro Ala Leu Pro
1

<210> SEQ ID NO 88
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 88

Trp Tyr Pro His
1

<210> SEQ ID NO 89
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 89

His Leu Arg Val
1

<210> SEQ ID NO 90
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 90

His Met Pro Arg
1

<210> SEQ ID NO 91

<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 91

Pro Val Ser Ile
1

<210> SEQ ID NO 92
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 92

Tyr Met Asn Asn
1

<210> SEQ ID NO 93
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 93

His Lys Leu Asn
1

<210> SEQ ID NO 94
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 94

Pro His Leu Pro
1

<210> SEQ ID NO 95
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified wtih biotin

<400> SEQUENCE: 95

Pro His Tyr Asn
1

<210> SEQ ID NO 96
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 96

Pro Leu Ala Gln
1

<210> SEQ ID NO 97
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 97

Val His Ala Trp
1

<210> SEQ ID NO 98
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified wtih biotin

<400> SEQUENCE: 98

Val His Asn Thr
1

<210> SEQ ID NO 99
<211> LENGTH: 4
<212> TYPE: PRT
<213> ORGANISM: Artificial Sequence
<220> FEATURE:
<223> OTHER INFORMATION: biotin-modified peptide
<220> FEATURE:
<221> NAME/KEY: MISC_FEATURE
<222> LOCATION: (1)..(1)
<223> OTHER INFORMATION: modified with biotin

<400> SEQUENCE: 99

Pro Phe Val Gln
1

<210> SEQ ID NO 100
<211> LENGTH: 24
<212> TYPE: DNA
<213> ORGANISM: Artificial Sequence
<220> FEATURE:
<223> OTHER INFORMATION: sequence identified in panning of a mixed-modification library (using streptavidin)

<400> SEQUENCE: 100 tctcctttg tgcagggcgg tggc 24

<210> SEQ ID NO 101
<211> LENGTH: 4
<212> TYPE: PRT
<213> ORGANISM: Artificial Sequence
<220> FEATURE:
<223> OTHER INFORMATION: control peptide
<220> FEATURE:
<221> NAME/KEY: MISC_FEATURE
<222> LOCATION: (1)..(1)
<223> OTHER INFORMATION: modified with sulfonamide

<400> SEQUENCE: 101

Gly Gly Gly Gly
1

<210> SEQ ID NO 102
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 102

Phe Val Val Arg
1

<210> SEQ ID NO 103
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 103

Thr Arg Pro Ala
1

<210> SEQ ID NO 104
<211> LENGTH: 4
<212> TYPE: PRT
<213> ORGANISM: Artificial Sequence
<220> FEATURE:
<223> OTHER INFORMATION: sulfonamide-modified peptide
<220> FEATURE:
<221> NAME/KEY: MISC_FEATURE
<222> LOCATION: (1)..(1)
<223> OTHER INFORMATION: modified with sulfonamide

<400> SEQUENCE: 104

Tyr Gln Tyr Arg
1

<210> SEQ ID NO 105
<211> LENGTH: 4
<212> TYPE: PRT
<213> ORGANISM: Artificial Sequence
<220> FEATURE:
<223> OTHER INFORMATION: galactose-modified peptide
<220> FEATURE:
<221> NAME/KEY: MISC_FEATURE
<222> LOCATION: (1)..(1)
<223> OTHER INFORMATION: modified with galactose

<400> SEQUENCE: 105

Pro Ala Pro Thr
1

<210> SEQ ID NO 106
<211> LENGTH: 4
<212> TYPE: PRT
<213> ORGANISM: Artificial Sequence
<220> FEATURE:
<223> OTHER INFORMATION: glucose-modified peptide
<220> FEATURE:
<221> NAME/KEY: MISC_FEATURE
<222> LOCATION: (1)..(1)
<223> OTHER INFORMATION: modified with glucose

<400> SEQUENCE: 106

Ser Ile Tyr Gly
1

<210> SEQ ID NO 107
<211> LENGTH: 4
<212> TYPE: PRT
<213> ORGANISM: Artificial Sequence
<220> FEATURE:
<223> OTHER INFORMATION: xylose-linked peptide
<220> FEATURE:
<221> NAME/KEY: MISC_FEATURE
<222> LOCATION: (1)..(1)
<223> OTHER INFORMATION: linked with xylose

<400> SEQUENCE: 107

Ala Leu Arg Val
1

<210> SEQ ID NO 108
<211> LENGTH: 4
<212> TYPE: PRT
<213> ORGANISM: Artificial Sequence
<220> FEATURE:
<223> OTHER INFORMATION: rhamnose-conjugated peptide
<220> FEATURE:
<221> NAME/KEY: MISC_FEATURE
<222> LOCATION: (1)..(1)
<223> OTHER INFORMATION: conjugated with rhamnose

<400> SEQUENCE: 108

Ile Trp Val Arg
1

<210> SEQ ID NO 109
<211> LENGTH: 15
<212> TYPE: DNA
<213> ORGANISM: Artificial Sequence
<220> FEATURE:
<223> OTHER INFORMATION: deep-sequencing variable region

<400> SEQUENCE: 109
agtccgccgc cgccg 15

<210> SEQ ID NO 110
<211> LENGTH: 15
<212> TYPE: DNA

-continued

```
<213> ORGANISM: Artificial Sequence
<220> FEATURE:
<223> OTHER INFORMATION: deep-sequencing variable region

<400> SEQUENCE: 110

tctttaacca gccaa                                                    15


<210> SEQ ID NO 111
<211> LENGTH: 15
<212> TYPE: DNA
<213> ORGANISM: Artificial Sequence
<220> FEATURE:
<223> OTHER INFORMATION: deep-sequencing variable region

<400> SEQUENCE: 111

tctgtccccg aattc                                                    15


<210> SEQ ID NO 112
<211> LENGTH: 15
<212> TYPE: DNA
<213> ORGANISM: Artificial Sequence
<220> FEATURE:
<223> OTHER INFORMATION: deep-sequencing variable region

<400> SEQUENCE: 112

agtccgccgc cgcct                                                    15


<210> SEQ ID NO 113
<211> LENGTH: 15
<212> TYPE: DNA
<213> ORGANISM: Artificial Sequence
<220> FEATURE:
<223> OTHER INFORMATION: deep-sequencing variable region

<400> SEQUENCE: 113

tctccgccgc cgccg                                                    15


<210> SEQ ID NO 114
<211> LENGTH: 15
<212> TYPE: DNA
<213> ORGANISM: Artificial Sequence
<220> FEATURE:
<223> OTHER INFORMATION: deep-sequencing variable region

<400> SEQUENCE: 114

agtcctccgc cgccg                                                    15


<210> SEQ ID NO 115
<211> LENGTH: 15
<212> TYPE: DNA
<213> ORGANISM: Artificial Sequence
<220> FEATURE:
<223> OTHER INFORMATION: deep-sequencing variable region

<400> SEQUENCE: 115

tctcctccgc cgcct                                                    15
```

GENETIC ENCODING OF CHEMICAL POST-TRANSLATIONAL MODIFICATION FOR PHAGE-DISPLAYED LIBRARIES

CROSS-REFERENCE TO RELATED APPLICATIONS

This application claims priority to PCT/CA2015/051077 filed Oct. 22, 2015 entitled "GENETIC ENCODING OF CHEMICAL POST-TRANSLATIONAL MODIFICATION FOR PHAGE-DISPLAYED LIBRARIES"; and to U.S. Provisional Patent Application Ser. No. 62/067,183 filed on Oct. 22, 2014, the entire contents of which are hereby incorporated by reference.

FIELD

The present application pertains to the field of recombinant protein technology. More particularly, the present application describes a method for genetic encoding of chemical modifications in genetically-encoded libraries of chemically-modified peptides.

BACKGROUND

The generation of libraries of small molecules and selection of those molecules that bind uniquely to a target of interest is important for drug discovery. The production of genetically-encoded libraries, in which each library member is linked to an information template, such as DNA or RNA, makes it possible to process large chemical libraries without separating individual library members into individual solutions and reaction vessels. One can select target molecules from mixtures of genetically-encoded molecules and identify or amplify the selected molecule of interest using its information template.

Phage display is one example of a genetically-encoded library. (Scott et al., 1990). Phage display is a well known technique used in the analysis, display and production of protein antigens, especially human proteins of interest. Phage display is a process during which the phage, a bacterial virus, is made to expose or "display" different peptides or proteins including human antibodies on its surface. Through genetic engineering, peptides or proteins of interest are attached individually to a phage cell surface protein molecule (usually Gene III protein, g3p). In such a phage population (phage library), each phage carries a gene for a different peptide or protein—g3p fusion and exposes it on its surface. Through a variety of selection procedures, phages that "display" binders to specific target molecules of interest can be identified and isolated. These binders can include interaction partners of a protein to determine new functions or mechanisms of function of that protein, peptides that recognize and bind to antigens (for use in diagnosis and therapeutic targeting, for example), and proteins involved in protein-DNA interactions (for example, novel transcription factors).

The phage display technique can be very useful in discovery and development of pharmaceutical andlor diagnostic products. In phage display the entire phage binds and can be eluted from an immobilized target molecule. Since the phage remains infective it can inject its DNA into bacterial cells and is amplified. The main limitation of phage display, however, is the occurrence of non-specific adsorption of phages during the binding stage, which necessitates enrichment over several rounds and individually tailored washing and elution conditions. Phage display methods are usually restricted to the production of libraries, which can be encoded by direct DNA-RNA-protein information transfer. These methods are typically limited to linear sequences of peptides, made of only 20 natural amino acids.

RNA and ribosome display are other techniques known in the art that permit display of naturally-made peptides on information templates. The amplification of libraries of peptides attached to RNA requires an in vitro translation system to generate or reamplify the library. The generation and use of such translation systems can be expensive and time consuming. The use of self-replicating species such as phage, yeast, or bacteria simplifies amplification of libraries because each library member is amplified "spontaneously", when given the appropriate resources. For example, for phage displayed libraries, adding one phage to a simple culture broth with bacteria can produce an arbitrarily large population of phage for a very low cost.

Genetic encoding of small molecules has been proposed in the 1990s (Brenner et al., 1990) and several implementations of such encoding strategies have been developed by different groups, including Lerner and Janda (Scripps), Lu (Harvard) and Harbury (Stanford). The encoding of small-molecules developed by these groups, however, is significantly more complex than technologies for display of polypeptides. Further, encoding strategies can be extremely difficult in terms of synthesis and achieving rapid round-to-round iterations in the process.

Another example of small-molecule display technology is through the use of encoded display of molecules derived from peptides via enzymatic or chemical post-translational modifications (cPTM). Typically, these methods use organic synthesis on the peptides to make peptide derivatives. Unlike the display of arbitrary organic molecules, the display of peptide-derived molecules is generally simpler because it builds on readily-available genetically-encoded peptide libraries.

It is known that an entire peptide library can be modified by uniform chemical modification. Selection from the modified library and sequencing of the DNA yields peptide sequences from which the modified peptide derivatives can be made. Several methods exist which involve conversion of libraries of phage-displayed polypeptides to libraries of peptide derivatives.

US Patent Publication 2010/0317547 to Winter and Heinis, describes specific modifications of phage displayed by alkylation of cysteine residues.

US Patent Publication 2009/0137424 to Schultz et al, describes specific modifications of phage-displayed peptide libraries by dipolar cycloaddition on azido phenyl alanine (AzPhe).

Bulk biochemical methods, such as western blot and mass spectrometry, are often used, to quantify the amount of product obtained or to determine the success of generating the desired reaction products. In the absence of this characterization, the synthesis cannot be claimed to be reliable or reproducible. Reactions used for synthesis of such libraries of peptide derivatives have typically been validated using one phage clone or one purified peptide. The actual synthesis of libraries is typically done without characterization under conditions optimized for a peptide but the efficiency of such synthesis is unknown. The quality of the libraries generated by this method is, thus, usually unknown. While selection from these libraries can provide useful non-peptidic molecules, overall the efficiency of such selection is unclear. The characterization and improvement of reaction is important for developing new chemically-modified libraries US Patent Publication 2013/050083 to Derda et al, describes a method for quantification of such modifications and selection of new strategies for effective modification.

It has been shown that cPTM of mRNA- or phage-displayed peptides can have similar advantages as mRNAiphage display while allowing the selection of ligands that cannot be encoded by conventional ribosomal synthesis. Selection of cPTM-libraries is a rapidly growing method that has been used by lead discovery academic research groups, start-up companies (Peptidream, Ra Pharma, Bicycle therapeutics) and large pharmaceutical companies (e.g., Pfizer[5]). In drug discovery, the display of cPTM-peptides facilitates developing a class of drugs that combines the advantages of "small-molecule" and "biological"-classes of drugs. Due to their small size, peptide-derivatives can have tissue permeability akin to that of small molecules, while genetic selection allows for rapid discovery and optimization of these molecules.

One of the problems with cPTM-libraries is genetic encoding of the modifications. While it is possible to convert linear peptide libraries to cyclic (Kawakami et al., 2013; Josephson et al., 2005; Jafari et al., 2014), bicyclic (Heinis et al., 2009), or glycosylated (Ng et al., 2012) molecules, multiple modifications cannot be performed on the same library because the identity of modification cannot be traced.

The screening of identical libraries with different modifications is known but it is typically done by parallel modification of different libraries, their parallel panning and processing, and their parallel sequencing (Chen et al., 2014; Schlippe et al., 2012). If two or more chemical modifications are combined into one library, such mixed library is difficult to analyze because it is usually not possible to distinguish between modified phage particles. There is no information about modification on the genetic level and there are no obvious and universal strategies for encoding or decoding such modifications.

There exists a need to provide an effective method of identifying molecules for drug discovery.

This background information is provided for the purpose of making known information believed by the applicant to be of possible relevance to the present invention. No admission is necessarily intended, nor should be construed, that any of the preceding information constitutes prior art against the present invention.

SUMMARY

An object of the present invention is to provide a method for genetic encoding of chemical modifications in genetically-encoded libraries of chemically-modified peptides.

In accordance with an aspect of the present invention, there is provided a method of synthesizing a genetically-encoded chemical modification of a peptide library comprising: nserting, into multiple independent vectors in a substrate, a first set of gene sequences encoding one or more substantially similar peptide linkers; inserting, into each vector, a second set of gene sequences encoding a variable set of peptides; expressing and amplifying the first and second sets of gene sequences such that a translation product comprising the substantially similar linkers and variable peptides is synthesized; modifying the set of variable peptides by a modification; and combining the set of modified variable peptides to produce a library in which the modification is encoded genetically.

In one embodiment, the first set of gene sequences encodes peptide sequences comprising chemically-similar or identical amino acids, but are encoded by different nucleotide codons.

In one embodiment, the second set of gene sequences comprises a random genetic library that encodes a random peptide library of different chemical compositions. In another embodiment, the second set of gene sequences comprises a focused genetic library that encodes a focused sub-set of peptide sequences of different chemical compositions, such as those generated by random mutagenesis, for example. The second set of gene sequences may encode a chemical structure of a molecule, such as a small molecule including a carbohydrate, biotin, sulphonamide, and other small molecules that have known biological activity. The small molecules used for chemical modification or cross-linkers encoded by silent barcoding are diastereomers or enantiomers.

The modification can be a chemical or enzymatic modification of the set of peptides. In one embodiment, the chemical modification is an introduction of a different small molecule in any location of the displayed peptide using a site-specific chemical conjugation technique. The chemical modification, for example, can result in the formation of oxime at the N-terminal serine, alkylation of cysteine, or any suitable method to modify a peptide or protein in a specific location. The reaction may include those that insert one or more linkers, one or more cross-linkers or one or more chemical "staples" to convert a peptide into a macrocycle with one of more bridges. Thus, in one embodiment, the second set of gene sequence may encode a chemical structure of the linker, cross linker or chemical staple. The substrate can be a phage, mRNA, ribosome, bacteria, yeast or any other genetic display technology known in the art.

In accordance with another aspect there is provided a method of selecting a genetically-encoded chemical modification of a peptide library comprising: inserting, into multiple independent vectors in a substrate, a first set of gene sequences encoding one or more substantially similar peptide linkers; inserting, into each vector, a second set of gene sequences encoding a variable set of peptides; separately expressing the first and second gene sequences on the substrate such that one or more peptide libraries are synthesized; modifying each of the one or more peptide libraries separately; pooling the modified peptide libraries together to produce a library in which chemical modification is encoded genetically; and screening the chemically-modified peptide library to select a peptide with a desired chemical modification.

In accordance with another aspect there is provided a method of identifying a drug target comprising: preparing a genetically-encoded chemically modified peptide library as described herein and screening the library with a molecule to identify chemically modified peptides by sequencing of the sequence encoding the peptide linker and the sequence encoding the variable peptide.

In accordance with another aspect of the present application there is provided a method of synthesizing a genetically-encoded chemical modification of a peptide library comprising: inserting, into multiple independent vectors in a substrate, a redundant set of gene sequences encoding a peptide linker, such that gene sequences produce identical or closely related peptide sequences ("linkers") upon translation; inserting, into each vector, a second set of gene sequences encoding a genetically diverse insert, such that a diverse set of peptides ("library"), is expressed upon translation; expressing and amplifying the first and second gene sequences such that a translation product comprises non-variable linker and variable peptide library is synthesized; and modifying each peptide library by a distinct modification and combining multiple modified libraries to produce a library in which chemical modification is encoded genetically.

The present application relates to producing a series of genetic sequences that introduce identical transcriptional products. This is referred to herein as a "silent barcode". Large numbers of such sequences can be created due to the redundancy of the genetic code and the trinucleotide encoding of amino acids. For example, glycine (Gly) can be encoded by four different codons: GGT, GGC, GGG, and GGA, while a (Gly)n sequence can be encoded by $4^n$ codon combinations, where n is the number of amino acids in the sequence.

The present application uses chemical modification of phage libraries that are identical in their chemical composition but can be distinguished by genetic sequencing due to the presence of the "silent barcode".

Different phage that carry different "silent barcodes" are produced separately and modified by different chemical modifications. Pulling these modified libraries together creates a mixed library in which the peptide sequence can be traced by sequencing of the variable region and the modification can be traced by sequencing of the "silent barcode".

While the location of the "silent barcode" can vary, it is convenient to position it in the proximity of the variable genetic region that encodes a peptide library. This proximity facilitates subsequent identification by sequencing.

Silent barcoding is particularly practical for the encoding of a small number of modifications (<100). This is particularly advantageous for the selection of modified peptides. For example, there are 20-50 known structurally-diverse natural PTMs on proteins. This handful of PTMs greatly increases the structural and functional diversity of proteins in higher organisms. Similarly in a display of cPMT-peptides, every modification converts billion of linear peptides to billion of cyclic or bicyclic variants or modified variants. Changing the nature of the linker allows selecting different variants form the parent peptide space (Chen et al., 2014).

BRIEF DESCRIPTION OF THE FIGURES

FIG. 6 illustrates sequence preferences observed within a selected library.

FIG. 10 shows analytical data for sulfonamide-modified peptides.

FIG. 14 shows analytical data for carbohydrate-modified peptides.

DETAILED DESCRIPTION

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

The present application provides a method for genetically encoding chemical modifications of a phage-displayed peptide library. In one embodiment, this can be achieved by assigning the identity of modifications in translationally "silent barcodes". For example, there are 4 codons that encode Gly and $3^4$=81 different ways to encode a Gly-Gly-Gly (GGG) linker, which connects random peptide library to the pill protein of the phage. Thus, it is possible to construct 216 libraries identical on the chemical (translational) level and distinguishable on genetic level, modify these libraries separately and pool them to create a cPTM-library in which every cPTM can be traced genetically.

Silent barcodes can be introduced at any location within the phage, including translationally active and silent regions, auxiliary proteins not used in phage assembly or sequences excised from phage proteins (e.g. leader). However, in certain embodiments, it is typical to position silent barcodes within close proximity to the variable region to allow for simultaneous characterization of these two regions by DNA sequencing.

Figure 2:
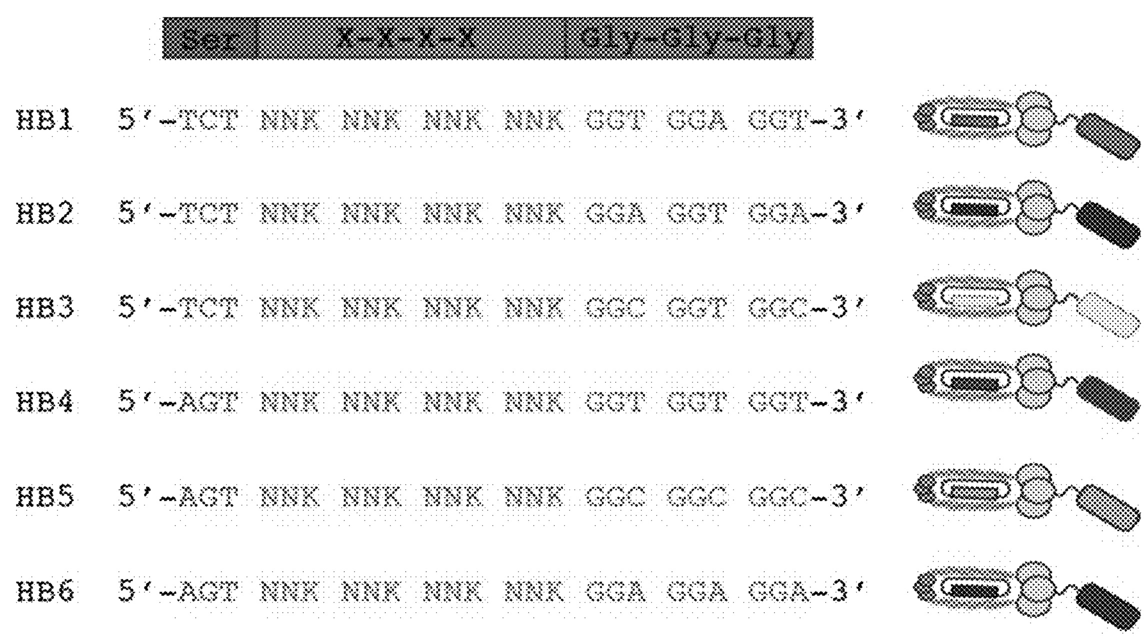
FIG. 2 illustrates specific examples of silent barcodes. Sequences for barcodes are selected such that one barcode cannot be converted to another barcode by a single substitution of one nucleotide, thus reducing the likelihood of introducing errors. In other words, barcode sequences typically do not reside within hamming distance (Hd)=1 from each other. Ideally, sequences that are Hd=2-3 from each other are selected.

For example, phage displaying the peptide sequence Ser-X-X-X-X-Gly-Gly-Gly (SEQ ID NO:10) were produced, where X is any amino acid and both Ser and Gly-Gly-Gly serve as the hidden barcode (HB) moiety. As shown in FIG. 2, specific examples of silent barcodes introduced in the regions adjacent to random tetra-amino acid library are provided. N is any nucleotide, K is G or T; NNK is a common combination of nucleotides uses to encode a random amino acid.

An unmodified library, and libraries carrying three different modifications, were combined to create libraries that contain four distinct N-terminal moieties (serine, biotin, sulfonamide and mannose). Panning and deep sequencing against four targets—streptavidin, carbonic anhydrase, ConA or BSA—was performed to illustrate that selection of modified peptides can be readily characterized by sequencing (see FIGS. 3 and 4).

Panning of libraries with multiplexed silent barcodes is limited to a single round of panning; however, analysis by deep-sequencing makes it possible to identify productive ligands even from a single round of panning. It is known in the art that the efficiency of one round of panning with deep sequencing can be matched to the efficiency of a multi-round screen with canonical Sanger sequencing.

Materials and Reagents

Chemical reagents and solvents were purchased from Sigma-Aldrich or Fisher Scientific unless noted otherwise. Synthesis of Mannose-hydroxylamine with 2-carbon linker has been described previously (Ng, et al.). Reagents for peptide synthesis were purchased from ChemPep; model peptides were synthesized using standard Fmoc solid phase synthesis as described below. Reactions were monitored by TLC which was carried out on silica gel 60 F254 (Merck) plates and visualized by UV-light (λ=254 nm) and/or by spraying potassium permanganate, anisaldehyde followed by heating. Flash column chromatography was performed using silica gel 60 (40-63 μm) using ISCO Teledyne Combiflash Rf instrument. The subsequent evaporation of solvents in vacuo was performed using IKA RV10 rotary evaporator. Proton (1H NMR) and carbon (13C NMR) nuclear magnetic resonance spectra were recorded on an Agilent/Varian VNMRS two channel 500 MHz or Agilent/Varian Inova two-channel 400 MHz spectrometer. The chemical shifts are given in part per million (ppm) on the delta scale. The solvent peak was used as reference values. For 1H NMR: CDCl3=7.24 ppm and for 13C NMR: CDCl3=77.16 ppm. The following abbreviations have been used: s, singlet; d, doublet; t, triplet; q, quadruplet, quin—quintet; m, multiplet; b, broad; d, doublet of doublets; ddd, doublet of doublet of doublets; td, triplet of doublets. Bovine carbonic anhydrase (BCA), biotin and lysozyme were obtained from Sigma-Aldrich Canada (Oakville, ON). The plasmid for natural core streptavidin, S4 (containing residues 13-139 of wildtype streptavidin, MW 13 271 Da) was a gift from Prof. P. Stayton (University of Washington) and expression of this protein is detailed below.

Synthetic Procedures

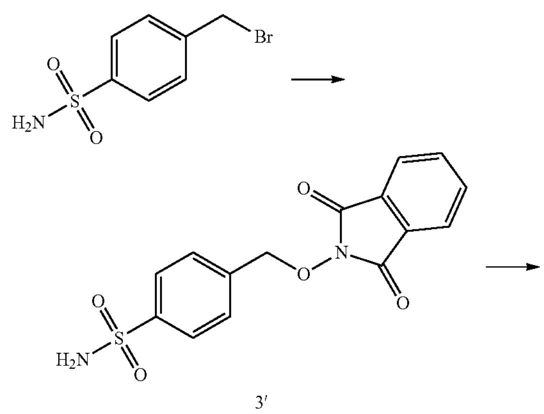

-continued

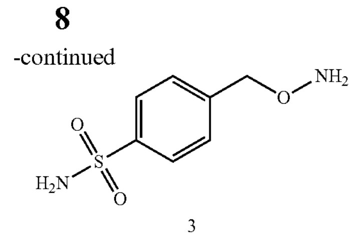

4-[[1,3-bis(oxidanylidene)isoindol-2-yl]oxymethyl] benzenesulfonamide (3')

4-sulfonamido-benzylbromide (Guillon et al., 2011) (460 mg, 1.84 mmol) and N-hydroxyphthalimide (360 mg, 1.2 eq) were dissolved in DMF (4 mL). $K_2CO3$ (276 mg, 2 mmol) was added and the mixture was stirred at 80° C. for 30 min then diluted with ethyl acetate, acidified with HCl, washed with water, concentrated to give copious precipitate (520 mg, 85%). $^{1}$H NMR (498 MHz, methanol-d4) δ ppm 7.92 (d, 2H, J 8.1 Hz, arom.), 7.82 (s, 4H, arom.); 7.71 (d, 2H, arom.), 4.82 (s, 2H, CH2). $^{13}$C NMR (126 MHz, methanol-d4) δ ppm 164.87, 145.69, 139.89, 135.90, 131.16, 130.22, 127.32, 124.39, 79.72. ESI-MS calculated for $C_{15}$H13N2O5S $(M+H)^+$: 333.0540, found: 333.0549.

4-(aminooxymethyl)benzenesulfonamide (3)

To a suspension of precursor 3' (200 mg, 0.6 mmol) in hot MeOH (2 mL) hydrazine hydrate was added (0.1 mL) (Kitov et al.). After 30 min the mixture was concentrated and purified using silica gel chromatography (DCM-5% MeOH) to give the title product (105 mg, 61%). $^{1}$H NMR (498 MHz, methanol-d4) δ ppm (d, 2H, J 8.1. Hz, arom.); 7.51 (d, 2H, arom.), 4.73 (s, 2H, CH2). $^{13}$C NMR (126 MHz, methanol-d4) δ ppm 144.32, 143.76, 129.37, 127.24, 77.75. ESI-MS calculated for C7H9N2O3S $(M-H)^-$: 201.0339, found: 201.0339.

Synthesis of Peptides on Solid Support

Rink Amide AM resin (200 mg, 0.91 mmol/g, 0.18 nimbi) was weighed into a Poly-Prep® chromatography column. The column was set up on a vacuum manifold. The manifold was equipped with a three-way stopcock that allows draining of the solvent by vacuum filtration and agitation of the resin by nitrogen bubbling (Kim et al., 2011). CH2Cl2 (3 mL) was added to the dried resin for swelling. After 15 min, the solvent was drained by vacuum aspiration. The resin was washed with. DMF (3 mL) and the protective Fmoc group was cleaved with 20% (v/v) piperidine in DMF (3 mL) for 1 min. The treatment was repeated for 10 min using fresh 20% (v/v) piperidine in DMF (3 mL). The resin was washed with DMF (4-3 mL). Fmoc-protected amino acid (0.73 mmol, 4 eq.) in DMF (1 mL) and HBTU (276 mg, 0.73 mmol, 4 eq.) in DMF (1 mL) was added to the resin followed by N,N-diisopropylaminoethylamine (DIPEA, 0.25 mL, 1.46 mmol, 8 eq.). After 30 min of agitation with nitrogen, the reagents were removed by vacuum aspiration and the resin was washed with DMF (4-3 mL). The Fmoc-deprotection, amide coupling, and washing steps were repeated consecutively as described above to elongate the peptide sequence. After final Fmoc deprotection, the resin was washed with DMF (5-3 mL), followed by $CH_2Cl_2$ (5-3 mL). The resin was left on the manifold for 10 min to dry under the vacuum. A cleavage cocktail containing TEA/H2O/phenol/triisopropylsilane [3 mL, 85/5/5/5 (v/v/w/v)] was added to the resin. The column was left on a rocker for 2 h to cleave the peptide then the solution was collected and the resin was rinsed with TEA (1 mL). The combined cleavage mixture was added dropwise to ice cold diethyl ether (20 mL) in a 50 mL centrifuge tube. The mixture was incubated on ice for 30 min then centrifuged for 5 min at 3000 rpm. Supernatant was decanted and the precipitates were resuspended in cold diethyl ether (10 mL). The centrifugation and washing steps were repeated 2 times. The precipitates were air-dried and then left under vacuum overnight. Typical yield: 50-150 mg.

Crude peptide (40 mg) was dissolved in DMF (0.25 mL) and 0.1% aqueous TEA (0.25 mL). The solution was injected into a semi-preparative C18-HPLC system. A gradient of solvent A (MQ deionized water, 0.1% (v/v) TEA) and solvent B (MeCN, 0.1% (v/v) TFA) was run at a flow rate of 12 mL/min as shown below.

| Time (min) | Eluent B (%) |
|---|---|
| 0 | 2 |
| 2 | 2 |
| 26 | 35 |
| 27 | 100 |
| 29 | 100 |
| 30 | 2 |

The fractions containing target peptides were identified using mass spectrometry either by MALDITOF of ESI LCMS. MeCN was removed by evaporation under reduced pressure. The aqueous solution was lyophilized to yield the peptide as white powder (20-32 mg). All peptides were used for synthesis of peptide conjugates and characterization was performed after the synthesis of the conjugate.

Synthesis of Sulfonamide Peptides

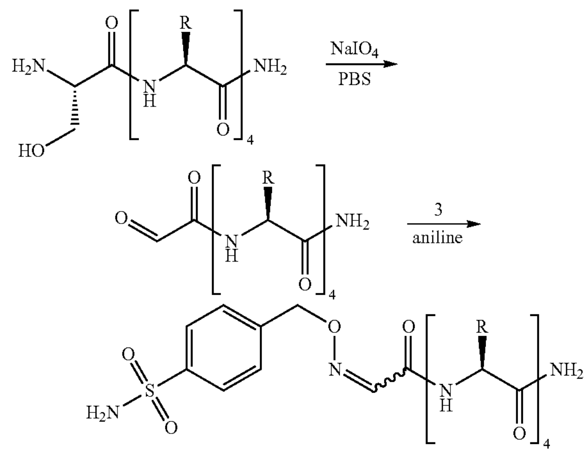

Synthesis was adapted from Ng et al (2012), with minor modifications. In one example of the procedure using H2N-SWYKL-CONH2 peptide (SEQ ID NO:1): the peptide (6.9 mg, 10 μmol, 1 eq.) was dissolved in DMF (0.25 mL) followed by the addition of 200 mM MOPS (0.25 mL, pH 7.0). The solution was added to a 1.5-mL microcentrifuge tube containing aqueous solution of sodium periodate (60 μL, 42.6 mg/mL, 12 μmol, 1.2 eq.). The reaction mixture was incubated for 10 min at RT. To quench the oxidation, solid glutathione was added (GSH, 37 mg, 120 μmol, 12 eq.) and mixed instantly to prevent buildup of free iodine (brown color appears momentarily upon GSH addition). After incubation for 10 min at RT, 4-(aminooxymethyl)benzenesulfonamide (3) (2.6 mg, 20 μmol, 2 eq.) dissolved in DMF (60 μL) was added to the reaction mixture followed by 200 mM anilinium acetate (0.25 mL, pH 4.7). The oxime ligation was carried out for 30 min at RT. The reaction mixture was injected into a semipreparative C18-HPLC system. HPLC purification was carried out as described above for crude peptide to yield the product as a white fluffy powder (40-70% isolated yield) after lyophilization. The purity of the product was determined with an analytical C18-HPLC system (flow rate: 1 mL/min) using a gradient of solvent A (MQ water, 0.1% (v/v) TFA) and solvent B (MeCN, 0.1% (v/v) TFA) as shown below.

| Time (min) | Eluent B (%) |
|---|---|
| 0 | 2 |
| 2 | 2 |
| 16 | 40 |
| 17 | 100 |
| 19 | 100 |
| 20 | 2 |

The product SA-WYKL (SEQ ID NO:2) was further characterized with LCMS and HRMS (ESI). Analytical data for all sulfonamide conjugates can be found below.

Construction of Silent Barcode Phage Display Libraries.

This protocol is modified from Ng et al. The anti-sense strand of the DNA oligonucleotide libraries were purchased from Integrated DNA Technologies with the following sequences (3'→5'):

```
                                        (SEQ ID NO: 3)
3'-GGGCCCATGGAAAGATAAGAGTGAGAAGA(NNM)4
CCACCTCCAAGCCGGCCCGCG-5'
                                        (SEQ ID NO: 4)
3'-GGGCCCATGGAAAGATAAGAGTGAGAAGA(NNM)4
CCTCCACCTAGCCGGCCCGCG-5'
                                        (SEQ ID NO: 5)
3'-GGGCCCATGGAAAGATAAGAGTGAGAAGA(NNM)4
CCGCCACCGAGCCGGCCCGCG-5'
                                        (SEQ ID NO: 6)
3'-GGGCCCATGGAAAGATAAGAGTGAGATCA(NNM)4
CCTCCTCCTAGCCGGCCCGCG-5'
```

200 pmol of each library was annealed with 3 molar equivalents of a short primer with the sequence 5'-CATGCCCGGGTACCTTTCTATTCTC-3' (SEQ ID NO:7) and extended by 15 U Klenow fragment (# EP0051, Thermo Scientific) in 1× of the provided reaction buffer and 50 μM dNTPs. The double-stranded library was purified by standard ethanol precipitation and resuspended in DNase-free water or TE buffer. The libraries were treated with KpnI and EagI FastDigest restriction enzymes (# FD0524 and # FD0334, Thermo Scientific) according to manufacturer recommendations and purified by 2% EGel® SizeSelect™ gel (Life Technologies). M13KE bacteriophage double-stranded DNA (dsDNA) was isolated from a single phage clone originating from the Ph.D.-12 phage display library (New England BioLabs) using the GeneJET Plasmid Miniprep Kit (Life Technologies) and similarly treated with KpnI and EagI FastDigest restriction enzymes, according to manufacturer instructions. The resulting DNA was purified by 0.7% agarose gel purification followed by gel extraction by GeneJET Gel Extraction Kit (Thermo Fisher Scientific, Waltham, Mass., USA). A 1:30 molar ratio of cut M13KE vector and library duplex was ligated by 400 U of T4 DNA ligase (New England BioLabs) at 16° C. overnight. Ligated DNA was purified by ethanol precipitation and re-suspended in DNase-free H2O and transformed using the Gene Pulser Xcell™ Electroporation System, 2 mm GenePulser/MicroPulser Electroporation Cuvettes (all from BioRad) with the settings 2500 V/400 Ohm/46 μF and commercially available F(+) TG1 electrocompetent cells and recovery media (Lucigen, Middleton, Wis., USA). Transformed cells were allowed to recover in the provided recovery media for 15 min at 37° C., 225 amplification for 4.5 hours. Phage were collected by PEG/NaCl precipitation from supernatant of culture, titered, and stored in MOPS buffer, pH 7.4.

Chemical Modification of the Phage Libraries.

The following protocol was modified from Ng et al (2015, 2012). A ~$10^{11}$ PFU/mL solution of phage library was oxidized with 0.06 niM sodium periodate (e.g. 1 μL of 6 mM sodium periodate into 99 μL of phage in PBS) for 5 min at RT in the dark and quenched with 0.5 mM glutathione (e.g. 1 μL of 50 mM glutathione) for 10 min at RT. To monitor the oxidation, a small portion of the oxidized library was treated with aminooxy-biotin and captured by biotin-capture assay as previously described (Ng et al., 2012). Typically, 60% of the fractions of phage library were successfully oxidized. Oxidized phage library was then modified with an equivalent volume of hydroxylamine conjugate (4-(aminooxymethyl)benzenesulfonamide, 2-(aminooxy)ethyl α-D-mannopyranoside, or aminooxybiotin, 2 mM solution in 200 mM anilinium acetate buffer, pH 4.7). The reaction mixtures were incubated for 1 h at RT, followed by dialysis against MOPS buffer to remove excess reagents (4° C., 1 mM, pH 7.3, three buffer changes over 18 h, 10K MW cut-off). To quantify the reaction efficiency, a small portion of the library was treated with aminooxy-biotin following oxime ligation and captured by biotin-capture assay as previously described (Ng et al., 2012). Typically, 55% of the fractions of phage library were successfully modified with the reagents.

Panning of Modified of Mixed-Modified Phage Libraries

The panning protocol was adapted from Ng et al with minor modifications.

Preparation of Targets:

Designated wells of a flat bottom 96-well Costar plate were coated with 100 μL of 10 μg/mL streptavidin, concanavalin A, bovine carbonic anhydrase II or BSA in MOPS buffer (20 mM, pH 7.4). Each target was coated in triplicate wells. The plate was sealed and incubated overnight at 4° C. The plate was then blocked for 1 h with a blocking solution (2% w/v BSA, 20 mM MOPS, pH 7.4) and washed using a 405™ Touch Microplate Washer (BioTek) as follows: 300 μL of wash buffer (0.1% w/v Tween-20, 20 mM MOPS, pH 7.4) followed by a 5 s shake and 30 s soak, repeated for a total of 10 cycles.

Preparation of Libraries.

The libraries were chemically modified the day before panning using the protocol described above. The following libraries were used in the model panning assay: B1 (DMannose), B2 (Unmodified), B3 (Biotin), and B4 (Sulfonamide). Libraries were combined in a 1:1:1:1 ratio at approximately $1\times10^{11}$ PFU/mL of each library. In a control panning experiment, B1, B2, B3 and B4 library were used individually, Panning Steps.

The mixed modified library (MIX) or individual libraries (B1-B4) were diluted to approximately $10^9$ PFU/mL in binding buffer (2% w/v BSA, 0.2% w/v Tween-20, 20 mM MOPS, pH 7.4) and distributed at 100 μL per well, at ~$1\times10^8$ PFU/well concentration.

After incubation for 1 h at RT, the plate was washed again using the same washing protocol. Bound phage was detached from the plates by elution buffer (0.2 M glycine-HCl, pH 2.2, 0.1% w/v BSA) for 9 minutes; the eluted solution was neutralized with M Tris-HCl, pH 9.1, The eluted phage solution was quantified by plaque forming assay. Titer of panning with individually-modified libraries were used to validate the presence of specific modifiers on these libraries (see FIG. 4).

Preparation for deep-sequencing (for MIX library only). The eluted phage was amplified for 4.5 h in 3 mL of LB supplemented with a 1:100 dilution of log phase *E. coli* K12 ER2738 (New England BioLabs). Single-stranded DNA (ssDNA) was isolated from the amplified phage using the QlAprep Spin M13 Kit (QIAGEN) and converted it to Illumina-compatible short dsDNA by PCR. Briefly, ~150 ng phage ssDNA was combined with 1× PCR buffer (New England BioLabs), 1 mM dNTPs, 0.5 μM each primer, and 0.5 μL Phusion High Fidelity DNA polymerase (New England BioLabs) in a total volume of 50 μL. Forward (F) and reverse (R) primer sequences, 5'→3':

```
F:
                                        (SEQ ID NO: 8)
5'-CAAGCAGAAGACGGCATACGAGATCGGTCTCGGCATTCCTGCTGAA

CCGCTCTTCCGATCTXXXXCCTTTCTATTCTCACTCT-3'

R:
                                        (SEQ ID NO: 9)
5'-AATGATACGGCGACCACCGAGATCTACACTCTTTCCCTACACGACG

CTCTTCCGATCTXXXXACAGTTTCGGCCGA-3'
```

The XXXX in the primer sequence denotes four-nucleotide-long barcodes used to trace multiple samples in one Illumina sequencing experiment. The temperature cycling protocol was as follows: 95° C. for 30 s, followed by 25 cycles of 95° C. for 10 s, 60.5° C. for 15 s and 72° C. for 30 s, and then a final extension at 72° C. for 5 min before holding at 4° C. The resulting dsDNA with Illumina compatible adapters was sequenced using the Illumina HiSeq platform (The Donnelly Sequencing Centre at The Donnelley Centre for Cellular and Biomolecular Research, University of Toronto) and analyzed as described in the subsequent section (Analysis of the Deep-sequencing Data).

Analysis of the Deep-Sequencing Data.

Analysis was adapted from Ng et al (2015) and Matochko et al., (2014) with minor modifications. Raw FASTQ data were processed using MatLab scripts described previously (Matochko et al.) with minor modifications to extract the copy numbers and enrichment ratios for significantly enriched sequences.

The following example illustrates calculation of the ratios for specific DNA sequences in The copy number of each read was offset by 1, to avoid division by zero, and then normalized by a total number of sequences in each column. The offset and normalized reads were averaged. R was calculated as the ratio of two averaged, normalized reads (eq. 1.1 and 1.2). Equation 1.3 describes specific example of calculation of one ratio for sequence SA-WYKL (SEQ ID NO:2) (SA is sulphonamide encoded by silent barcode). Note that all total number of sequences are in thousands of reads (i.e., 486 corresponds to 486,000 reads).

$$R_{12} = \frac{\sum \frac{(r_i^{<MIX:BCA>}+1)}{T_i^{<MIX:BCA>}}}{\sum \frac{(r_i^{<MIX:ConA>}+1)}{T_i^{<MIX:ConA>}}};\ R_{13} = \frac{\sum \frac{(r_i^{<MIX:BCA>}+1)}{T_i^{<MIX:BCA>}}}{\sum \frac{(r_i^{<MIX:Strep>}+1)}{T_i^{<MIX:Strep>}}}; \quad (1.1)$$

$$R_{14} = \frac{\sum \frac{(r_i^{<MIX:BCA>}+1)}{T_i^{<MIX:BCA>}}}{\sum \frac{(r_i^{<MIX:BSA>}+1)}{T_i^{<MIX:BSA>}}};\ R_{15} = \frac{\sum \frac{(r_i^{<MIX:BCA>}+1)}{T_i^{<MIX:BCA>}}}{\sum \frac{(r_i^{<MIX:amp>}+1)}{T_i^{<MIX:amp>}}}$$

$$R_0 = \sqrt{R_{12}^2 + R_{13}^2 + R_{14}^2 + R_{15}^2} \quad (1.2)$$

$$R_{12} = \frac{\sum \frac{(r_i^{<MIX:BCA>}+1)}{T_i^{<MIX:BCA>}}}{\sum \frac{(r_i^{<MIX:ConA>}+1)}{T_i^{<MIX:ConA>}}} = \frac{\frac{661+1}{486} + \frac{940+1}{515} + \frac{255+1}{568}}{\frac{0+1}{459} + \frac{0+1}{491} + \frac{0+1}{528}} = 596 \quad (1.3)$$

The present examples described herein focus on peptide libraries displayed on phage; however, other genetically-encoded libraries of peptides displayed on RNA, DNA, bacteria, yeast and other display systems known in the art may be used analogously.

Example 1

A Specific Implementation of Peptide Libraries with Silent Barcodes

The M13KE vector, which is used in popular commercially-available Ph.D.-7 or Ph.D.-12 libraries, was used as the foundation for the present design. However, other phage/phagemid vectors and other display platforms may be used.

Figure 1:
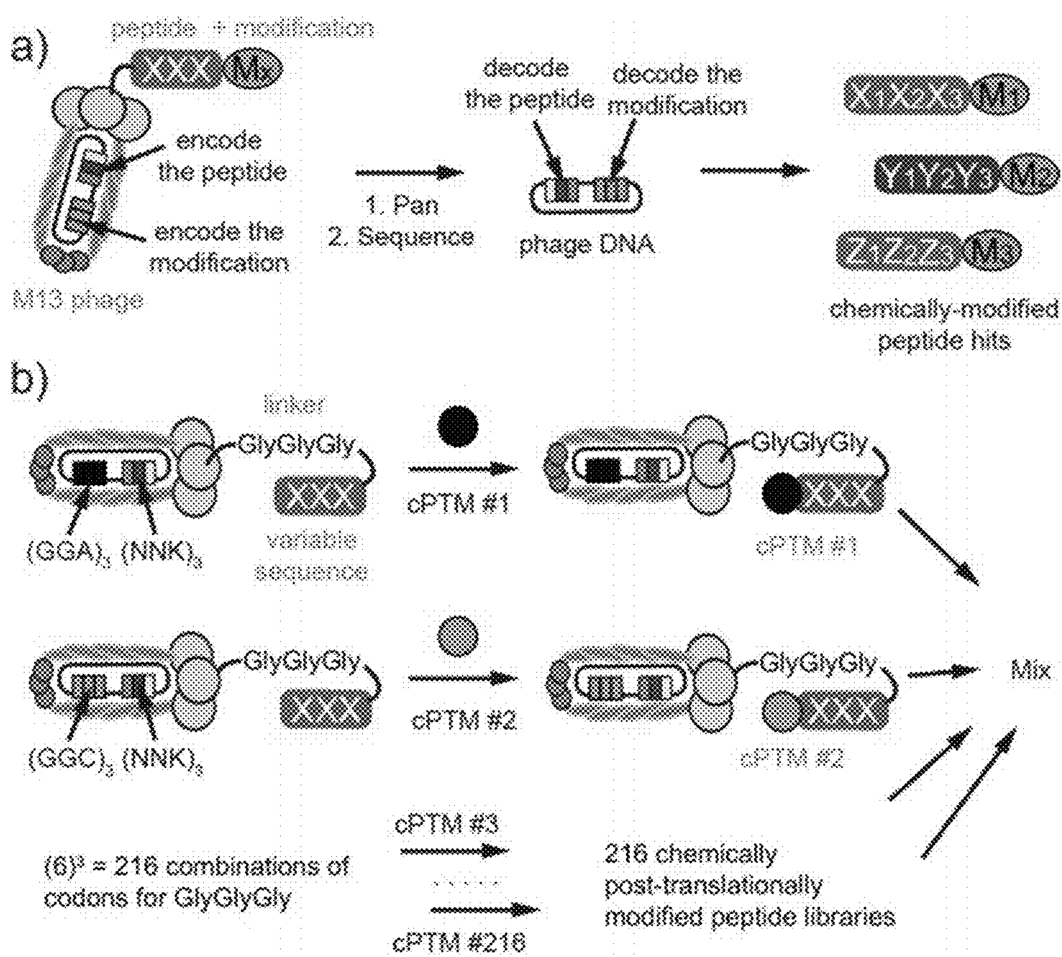
FIG. 1 provides a scheme for encoding which is specific to phage-displayed libraries of polypeptides. Analogous encoding by an adjacent random and silent barcode can be performed in any known-in-the art platform used for encoding and screening of polypeptide libraries.

Production of libraries with silent barcodes required no modifications to phage-library cloning: restriction enzyme cloning to introduce different variants of SXXXXGGG (SEQ ID NO:10) linker was (see FIG. 1 for specific DNA sequences). Since production steps are identical, multiplex production and creating 5-10 libraries at once can be achieved.

FIG. 2 shows specific examples of silent barcodes (SEQ ID NOs:11-16) introduced in the regions adjacent to random tetra-amino acid library. N is any nucleotide, K is G or T; NNK is a common combination of nucleotides uses to encode a random amino acid.

The efficiency of modification by each cPTM was determined as previously described (Ng et al., 2012). As each modification uses the same bond-forming process, the efficiency of modifications was similar.

The preparation of single-stranded phage DNA for Illumina sequencing required no modification, because COG and S regions of the library reside in close proximity to each other and can be sequenced as described previously (Matochko et al., 2012)

Example 2

Validation of the Barcode System with a Model Selection Assay Using Well-Defined Ligand-Target Pairs This example describes the modification of four barcoded phage libraries produced in Example 1 by three ligands that recognize three specific proteins. Ligand 1 is biotin that recognizes streptavidin (target 1). Ligand 2 is sulfonamide that recognizes carbonic anhydrase. Ligand 3 is mannose that recognizes concanavaline A (target 3). Modification 4 is the absence of any modification (i.e. non-modified peptide libraries). Target 4 (BSA-coated well) was introduced, such that it is not specifically recognized by any modifications.

Figure 3:
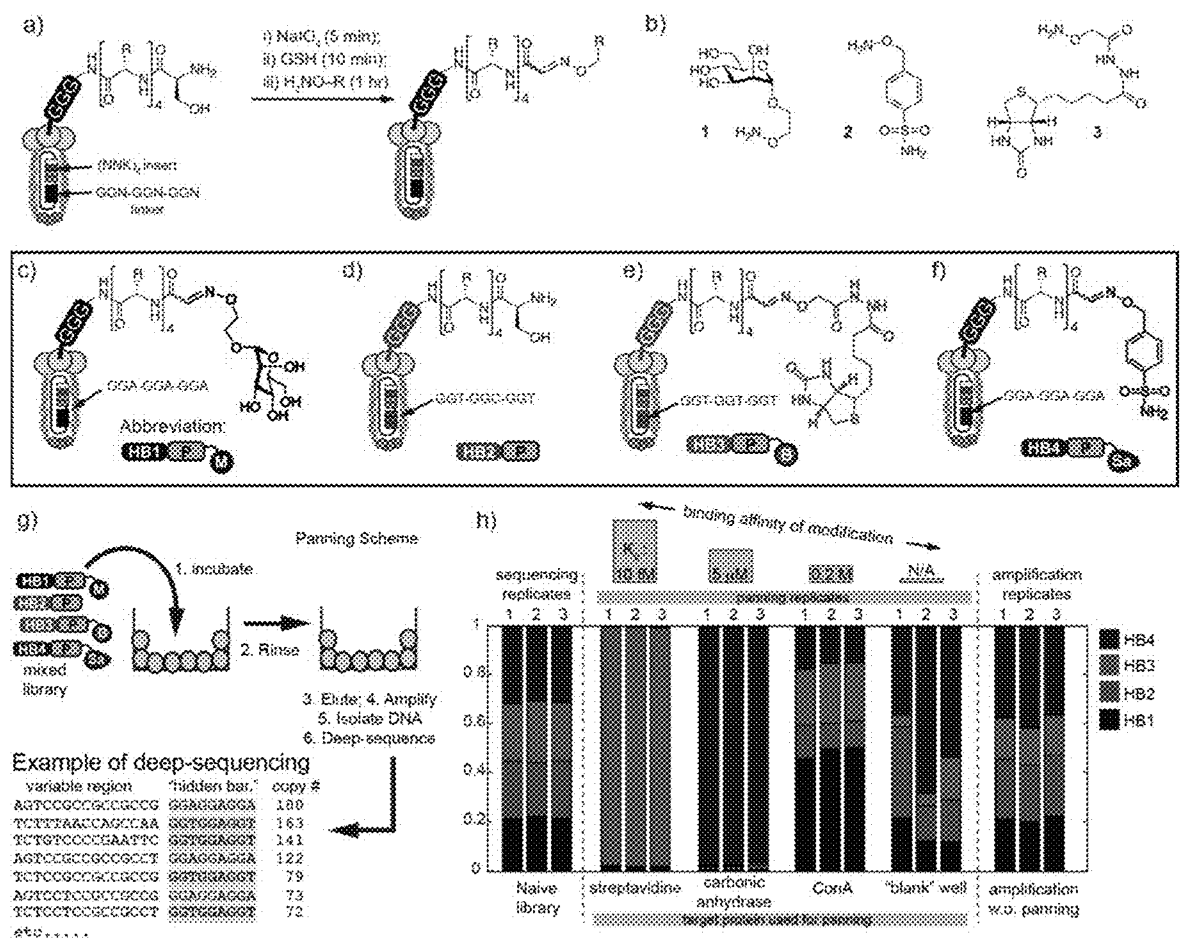
FIG. 3 illustrates modifications and selection against a matched target. Barcoded libraries are selected against the expected target. The selection strength follows the affinity of the ligands that anchor the library to the target protein.

A mixed library containing modifications 1, 2, 3, and 4 against targets 1, 2, 3, and 4 was panned. FIG. 3 illustrates a model selection assay of phage libraries with genetically encoded chemical modifications. In FIG. 3*a*, library phage were conjugated to compounds (FIG. 3*b*) through $NaIO_4$ oxidation of N-terminal serine and a short quenching step with GSH, followed by oxime ligation of the compound. FIG. 3*c-f* show exemplary chemical modifications: HB1-Mannose (FIG. 3*c*), HB2-no modification (FIG. 3*d*), HB3-biotin (FIG. 3*e*), and HB4-streptavidin (FIG. 3*f*). FIG. 3*g* illustrates a mixed library containing equal ratios of each modified library incubated with immobilized streptavidin, carbonic anhydrase, ConA or an uncoated well, followed by a rinsing step and acid elution. Eluted phage were amplified and processed for single-stranded phage DNA isolation and sequencing by Illumina ("variable regions", SEQ ID NOs: 109-115). FIG. 3*h* uses stacked-bar representation to show the relative abundance of the barcodes in phage libraries. Prior to selection, the library contained ~25:25:25:25 ratio of four barcodes. After selection on streptavidin, the ratio is ~1:97:1:1, with barcode #2 dominating the population while selection on carbonic anhydrase yields ratio 97:1:1:1 with barcode #1 dominating the population. Barcodes #1 and #2 encode populations with biotin and sulfonamide respectively. Selection on unrelated target that should not be recognized by any modification, such as selection against blank, BSA-coated plate, does not yield enrichment of any barcode or this enrichment is not reproducible from experiment to experiment. Finally, the barcoded phage library is stable and its composition is not changed when the library is allowed to amplify without any selection.

Figure 4:
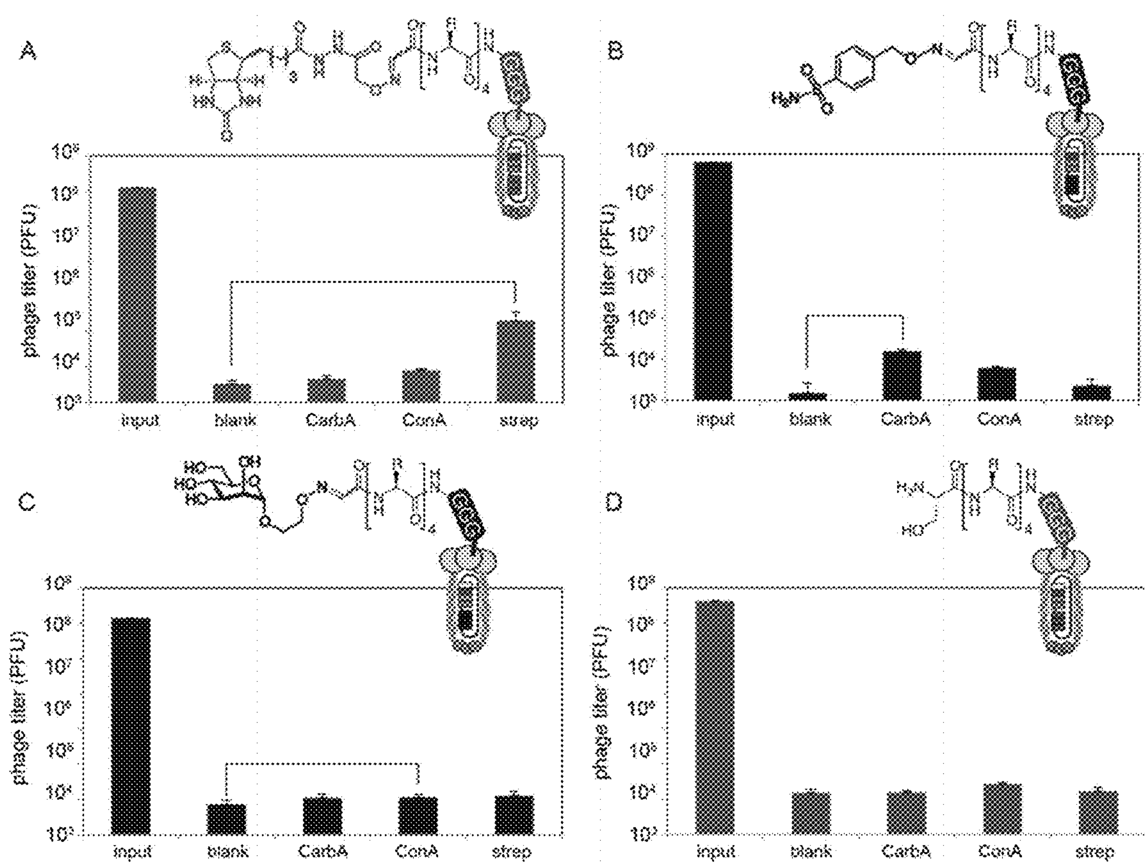
FIG. 4 illustrates the confirmation of the presence of chemical modifiers on phage displayed libraries.

FIG. 4 illustrates the confirmation of the presence of chemical modifiers: Biotin, Sulfonamide, D-Mannose, and unmodified on phage displayed libraries by measuring the input and output titers in panning of these phage libraries on the following four targets—streptavidin, bovine carbonic anhydrase II, concanavalin A, or BSA ("blank")—coated on 96-well plates. Biotin and sulphonamide modified libraries enrich significantly in the wells coated by the cognate targets (streptavidin and carbonic anhydrase). Enrichment of mannose-modified libraries on ConA was modest, similarly to what was observed previously (Ng, S., 2015).

FIG. 3*h* illustrates that deep sequencing of the selected libraries 1, 2, 3, and 4 confirmed significant abundance of phage with "matched" modification. For example, when panning on carbonic anhydrase, 95% of the selected phage library members carried a silent barcode that indicated presence of sulfonamide.

Figure 5:
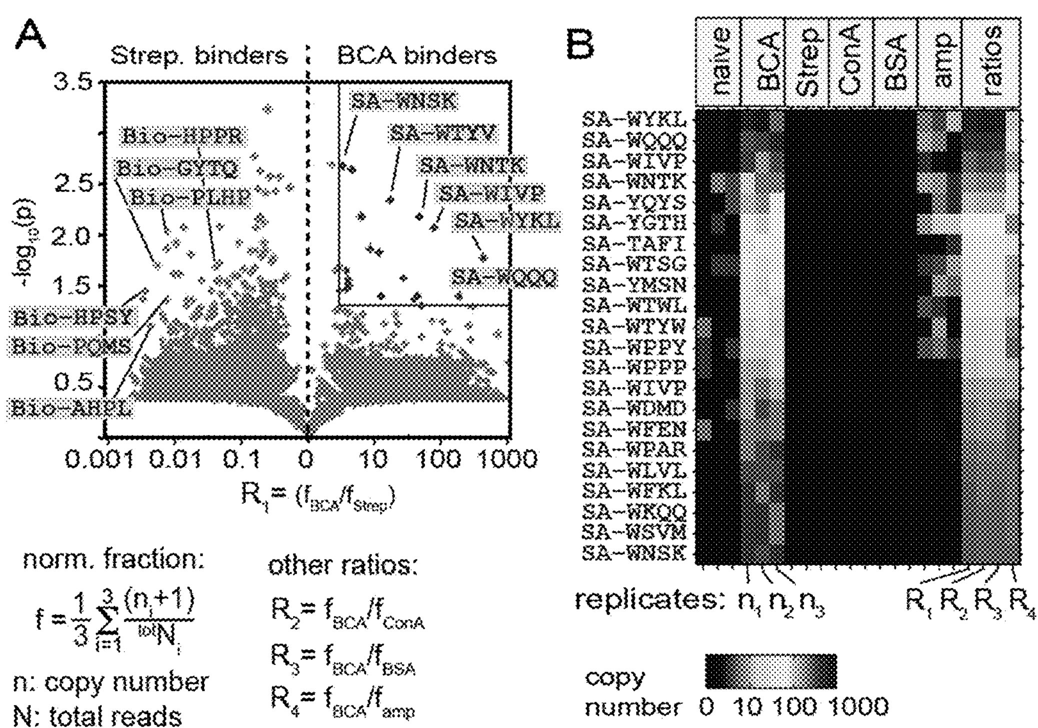
FIG. 5 illustrates the analysis of the enrichments in the selected library by ratiometric analysis.

FIG. 5 provides (A) a plot of ratio vs. p-value ("volcano plot") in a selection of barcoded libraries against BCA and streptavidin; ligands with R>3 and p<0.05 were enriched in panning on BCA; those with R<0.3 and p<0.05 were enriched in panning on streptavidin. Equations below show calculation of ratios R from normalized fractions of each sequence. Two enriched sets have different chemical modificationssulfonamide (SA) for BCA and biotin (Bio) for streptavidin—and different sequence motifs. FIG. 5 provides copy numbers and ratios for selected sequences (SEQ ID NOs:2 and 17-27). (B) Sequences (SEQ ID NOs:2, 23 and 25-43) significantly enriched in panning on BCA but not in four control panning experiments on ConA, BSA, streptavidin or during amplification without selection (all in triplicates). The heat map describes copy numbers determined by deep sequencing.

FIG. 5 demonstrates that panning of the library with multiple modifications enriched not only specific modifiers but also specific peptide sequences. Using previously published enrichment analysis (Ng, et al., 2015) SA-modified peptides were identified as sequences that were significantly enriched ($p<0.05$) in panning on BCA when compared to panning on an unrelated target (BSA, Streptavidin or ConA, FIG. 3A). As an additional control, we screened for and discarded fast-growing "parasite sequences" (Matochko, et al., 2014) that emerged from amplified library phage without panning. For each test-control pair, the analysis can be illustrated as a volcano plot (FIG. 4 compares selection against BCA to selection against streptavidin; additional volcano plots are in FIG. 6).

FIG. 6 illustrates specific DNA sequences, peptides and sequence motifs identified in panning of the same mixed-modification library (from FIG. 3 or FIG. 5) on carbonic anhydrase (A) (SEQ ID NOs:2, 23, 25-36, 40-64) and streptavidin (B) (SEQ ID NOs:18, 20-22, 65-100). Numbers represent normalized copy numbers of sequence in each panning experiment. "Blank" refers to well-coated with no target. "Naïve" refers to the library before selection and "Amplified" refers to the library amplified without any selection. "Ratio" represents a ratio of average copy number values.

The sequence copy number (abundance) in the library is illustrated, as measured by Illumina sequencing, in 12 different phage populations. Three of them, described in the first three columns, originate from panning on sulfonamide (SA), three from panning on blank, BSA-coated well, three samples represent the naïve (unselected) library and the last three represent library that was amplified without any selection. Deep sequencing revealed peptide motifs in the variable peptide region, which suggested that there are peptide sequences that synergize with chemical modification to provide increased affinity towards the target. By comparing the abundances in CA-selected samples with abundances in other experiments, sequences were identified that are preferentially enriched in selection against CA. It was observed that selection on CA peptides modified peptides that carry GGAGGAGGA barcode, which indicates that all peptides were modified by sulfonamide (SA). Furthermore, it is observed that only specific peptides sequences modified with SA are reproducibly selected whereas the other peptides modified by SA are not. Specifically, W-rich peptide sequences are selected for SA-modified libraries panned on carbonic anhydrase. The nature of the peptide sequence changes when the barcode and the target changes. For example, H-P-rich motifs are more preferentially selected on biotin-modified peptides selected against streptavidin.

Figure 7:
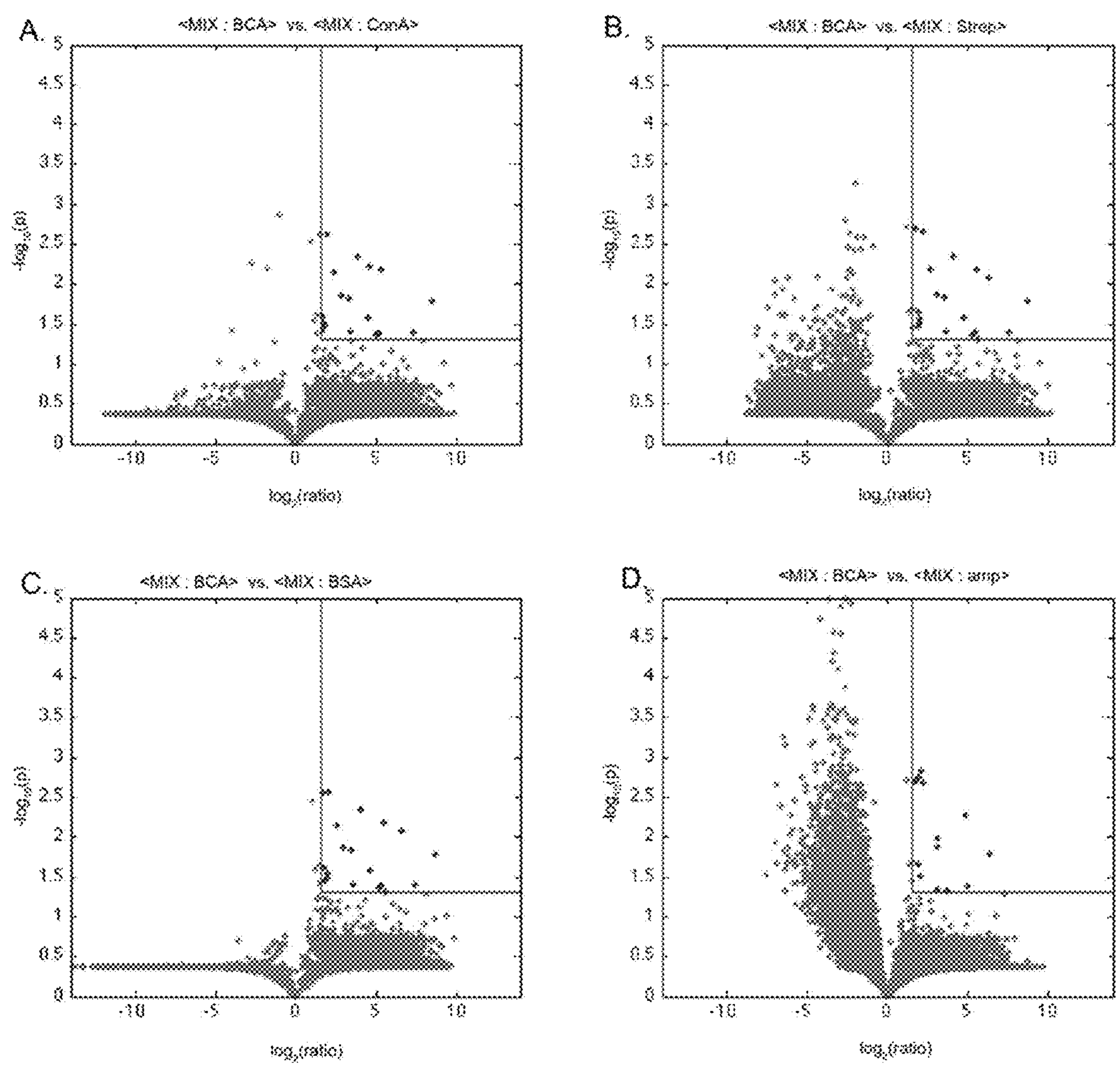
FIG. 7 shows volcano analysis of the copy number of peptides identified after panning and deep-sequencing of the mixed-modified libraries (MIX).

FIG. 7 shows a volcano analysis of the copy number of peptides identified after panning and deep-sequencing of the mixed-modified libraries (MIX) against Bovine Carbonic Anhydrase (BCA) and four additional controls. (A): MIX panned on BCA compared to MIX on ConA; (B): MIX panned on BCA compared to MIX on Streptavidin; (C): MIX panned on BCA compared to MIX on BSA; (D): MIX panned on BCA compared to MIX-library amplified without any panning. Normalized ratios (R) for each experiment were calculated as described above. P-values were calculated using normalized reads and one-tailed, unequal variance Student t-test. Blue lines define the thresholds used for selection: $p<0.05$ and $R>3$. All sequences that satisfy these criteria display sulfonamide barcodes.

Figure 8:
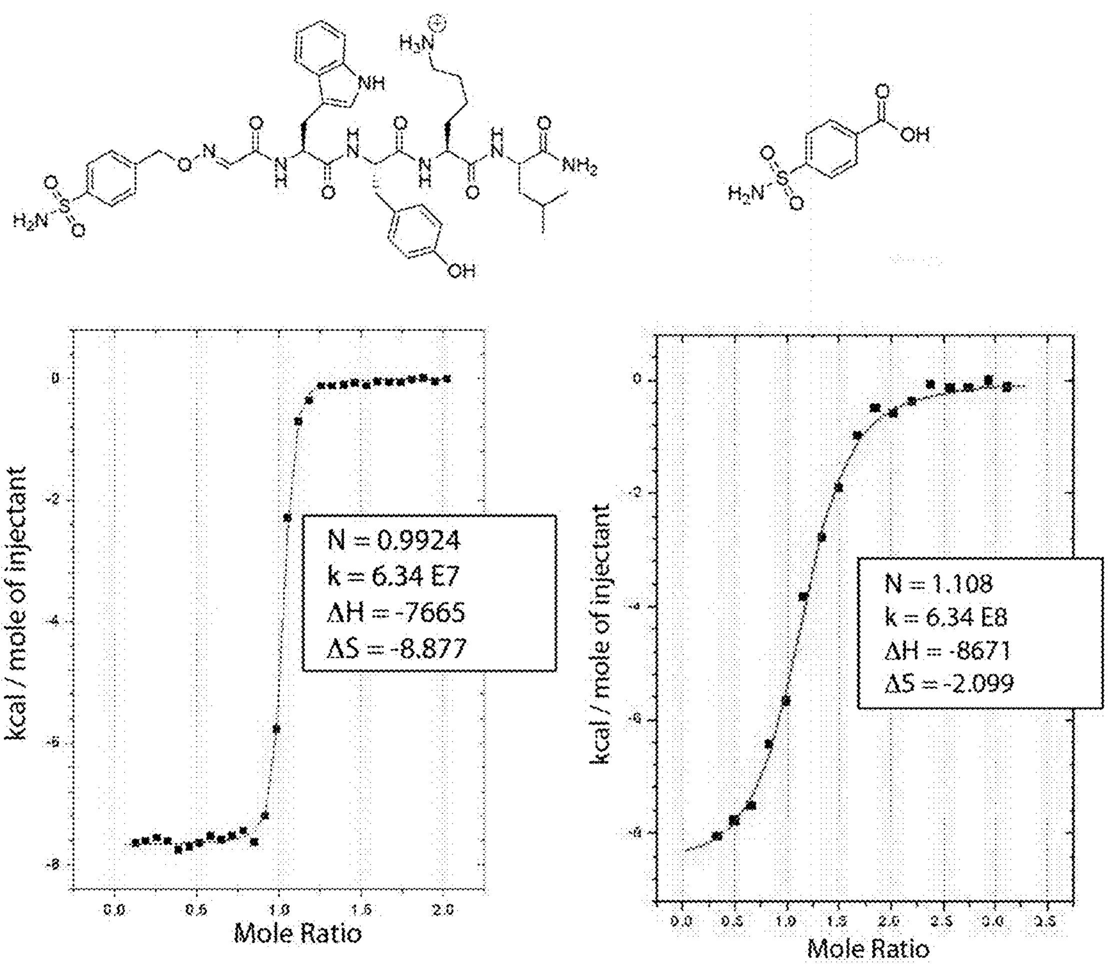
FIG. 8 shows exemplary ligands binding to the corresponding target. Peptide sulfonamide binds with 30 nM affinity.

FIG. 8 shows an example of binding of peptide-sulfonamide (left) and carboxy-sulfonamide (right) and to carbonic anhydrase. Binding constants are 1.6 uM and 30 nM respectively demonstrating 30-fold benefit for attaching the peptide moiety to sulfonamide.

Testing the peptide-sulfonamide by binding assays—isothermal titration calorimetry—validated that selected sequences indeed provide advantages over sulfomanide itself.

Figure 9:
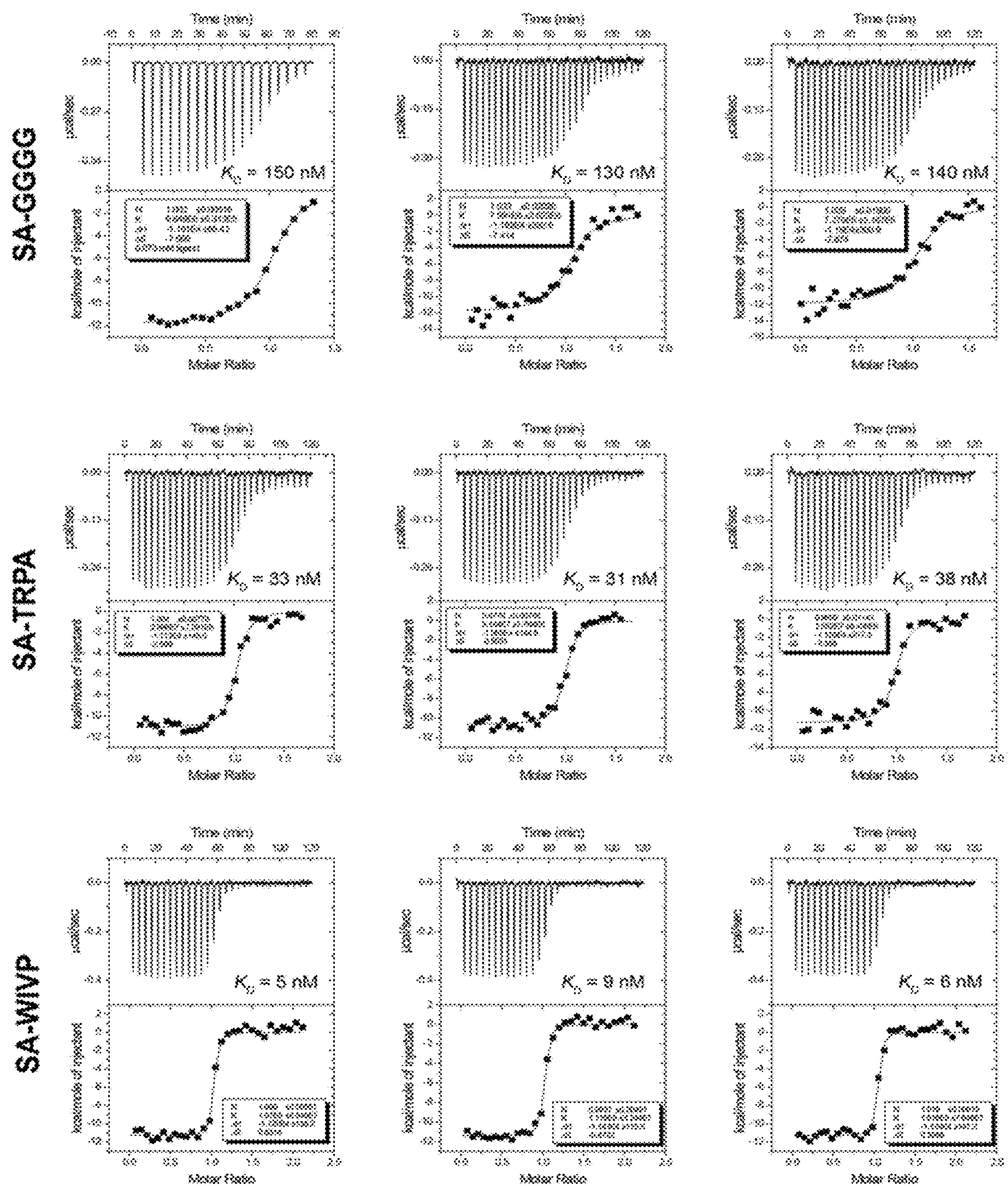
FIG. 9 provides additional raw ITC data of sulfonamide-peptide (SA-XXXX) binding to carbonic anhydrase.

FIG. 9 provides additional replicates of raw ITC data of sulfonamide-peptide (SA-XXXX) binding to carbonic anhydrase. Raw data obtained for 30 injections of ligands (20-95 μM) into a solution of carbonic anhydrase (2.5-12 μM) at 4-min intervals and 30° C. is shown. The integrated curve showed experimental points in microcalories per second and the best fit (-) to the single binding site model. The assay confirms that peptides selected in the screen, such as SA-WIVP (SEQ ID NO:26), have strong affinity as low as 5 nanomolar, which is significantly (30-fold) stronger than the affinity of the control peptide SA-GGGG (SEQ ID NO:101) (150 nanomolar).

FIG. 10 shows analytical data for sulfonamide-modified peptides. FIG. 10A is SA-WYKL (SEQ ID NO:2); FIG. 10B is SA-WQQQ (SEQ ID NO:27); FIG. 10C is SA-WIVP (SEQ ID NO:26); FIG. 10D is SA-WNTK (SEQ ID NO:25); FIG. 10E is SA-YQYS (SEQ ID NO:28); FIG. 10F is SA-WTSG (SEQ ID NO:31); FIG. 10G is SA-WTWL (SEQ ID NO:33); FIG. 10H is SA-WTYW (SEQ ID NO:34); FIG. 10I is SA-FVVR (SEQ ID NO:102); FIG. 10J is SA-TRPA (SEQ ID NO:103); FIG. 10K is SA-WPAR (SEQ ID NO:39); FIG. 10L is SA-YQYR (SEQ ID NO:104); FIG. 10M is SA-GGGG (SEQ ID NO:101).

Example 3

Validation of the Barcode System with a Selection Assay Using Structurally-Related Ligands (Monosaccharides that Differ by One Atom or One Chiral Center)

This example describes the modification of six barcoded phage libraries produced in Example 1 by six structurally related ligands: Glucose, galactose, rhamnose, xylose, mannose short-linker and mannose long-linker.

Figure 11:
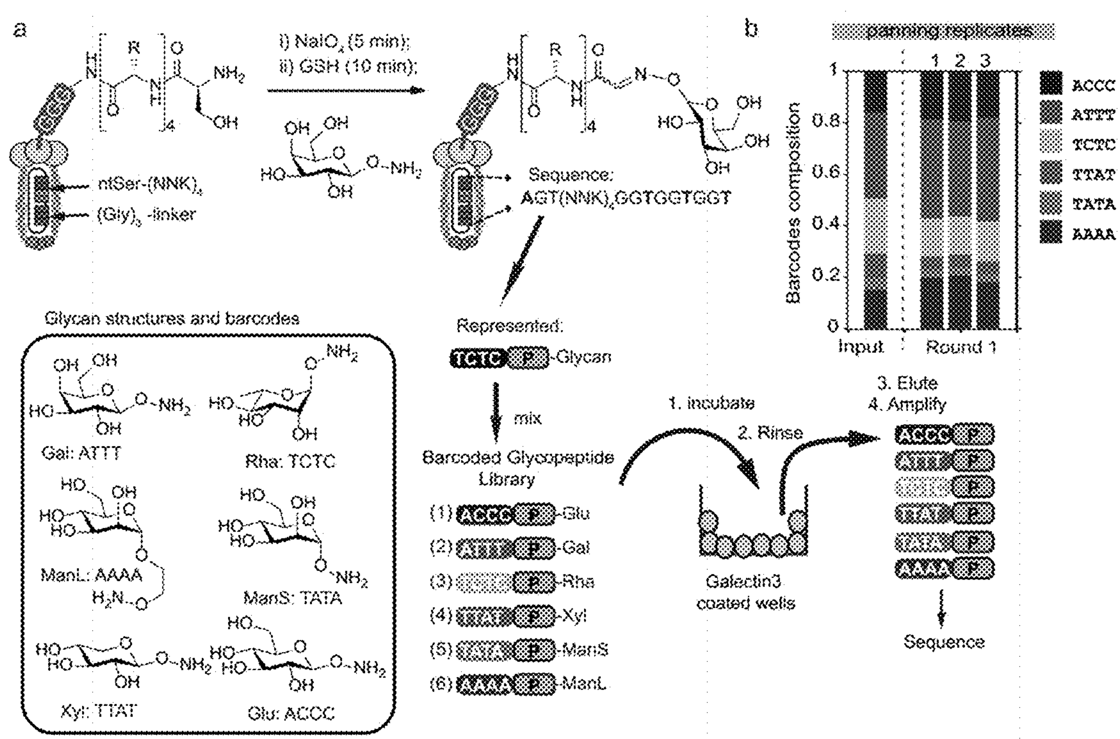
FIG. 11 shows a selection assay of phage libraries with various genetically encoded monosaccharides.

FIG. 11 shows a selection assay of phage libraries with six genetically encoded carbohydrates introduces by chemical conjugation. FIG. 11A illustrates library phage that were conjugated to compounds through $NaIO_4$ oxidation of N-terminal serine and a short quenching step with GSH, followed by oxime ligation of the compound. Glucose (1), galactose (2), rhamnose (3), xylose (4), mannose short-linker (5) and mannose long-linker (6), derivatives used for modification of the libraries. The figure shows a model panning assay, a mixed library containing defined ratios of each modified library was incubated with immobilized galectin 3, followed by a washing step and acid elution. Eluted phage were amplified and processed for a second round of selection where all barcoded libraries were uniformly decorated with galactose derivative. Single-stranded phage DNA was isolated for Illumina sequencing at round 1 and round 2. FIG. 11B shows an analysis of sequencing data. Phage eluted from galectin3 coated wells showed a pronounced binding preference for the corresponding protein target. Relative ratios of eluted phage correspond to the relative binding affinity of the modification for the target protein.

Panning these libraries against human Galectin-3 protein (Gal3) using a selection and deep-sequencing procedure similar to the procedures described in Example 2 found combinations of monosaccharides and tetramer peptides that bind to Gal3 when modified with Galactose, Glucose, Xylose and Rhamnose. The identity of monosacharides was decoded using "silent barcode" technology.

Figure 12:
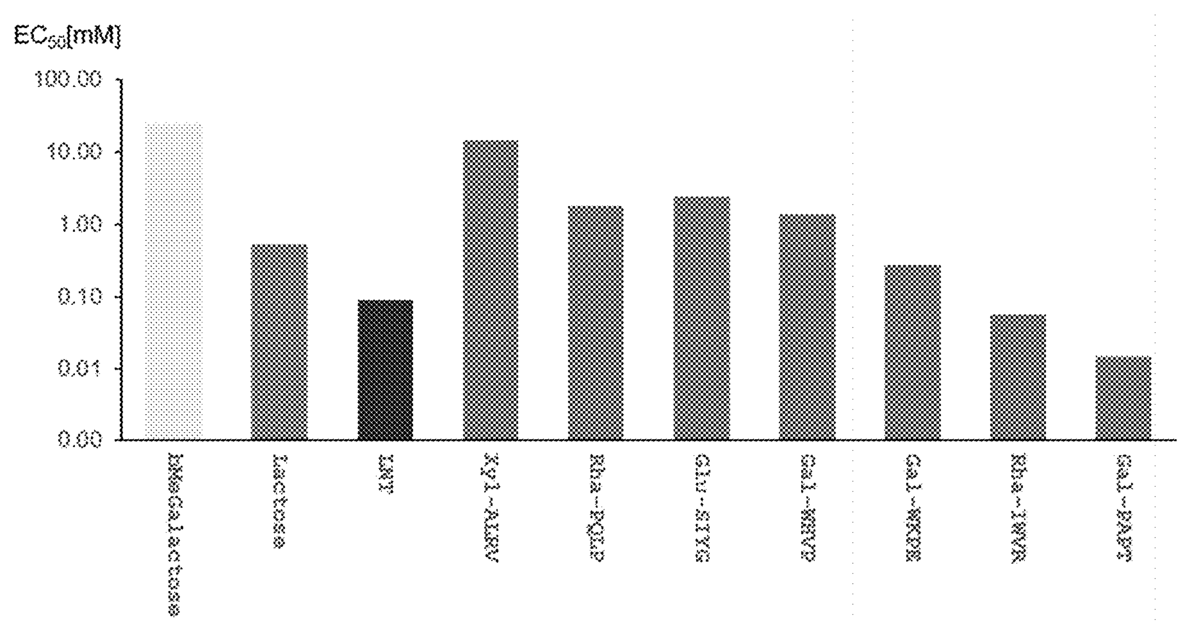
FIG. 12 shows activity of hits identified from genetically-encoded libraries of glycopeptides against Galactose-3.

Using an ELISA-like competition assay (FIGS. 12, 13), the binding activity of these glycopeptides to carbohydrate recognition domain (CRD) of the human Galectin-3 and their ability to compete with binding of Lactose-conjugated horseradish peroxidase (HRP), were validated (FIG. 12). As references, we used known Gal3 ligands, such as lactose, Methyl-β-D-galactopiranoside (MeGal) and tetrasaccharide Lacto-N-Tetraose (LNT).

In this screen, multiple combinations of Gal and tetrapeptides were found that may inhibit interaction of Gal3 and Lactose-HRP significantly stronger than MeGa (FIG. 11). The glycopeptide Gal-PAPT (SEQ ID NO:105) was the most potent hit. Its ability to inhibit HRP-Lac binding to immobilized Galectin-3 plates was 5 times better than LNT, 30 times better than the Lactose and >1500 times better than MeGal activity.

FIG. 12 illustrates an evaluation of activity of hits identified from genetically-encoded libraries of glycopeptides against Galactose-3. The assay measures that inhibitory constant (denoted as Effective concentrations of half-maximal response or EC50) of compounds in the inhibition of the interaction between soluble HRP-Lactose and surface-immobilized Galectin-3. The Galactose modified glycopeptide Gal-PAPT (SEQ ID NO:105) had the strongest inhibition activity EC50: 0.014 mM, which is significantly lower than EC50 os any of the controls. The results revealed a combination glucose and tetramer peptide (Glu-SIYG; SEQ ID NO:106) that binds to Gal3 and inhibits the binding of HRP-Lactose on Galectin 3 coated wells with 10 times higher potency than the control MeGal and it was similar to the affinity of Lactose (FIG. 12).

Figure 13:
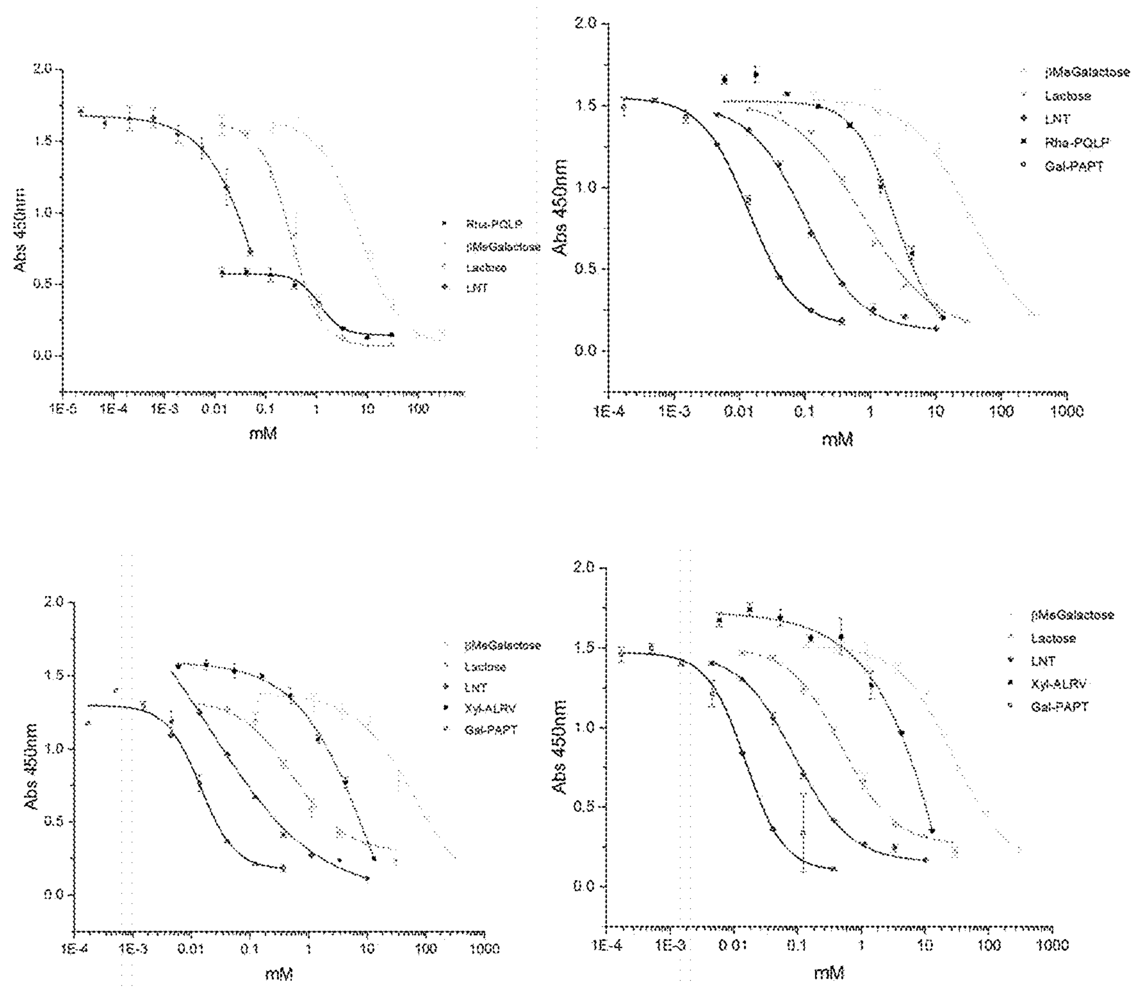
FIG. 13 shows raw data from experiments that measures the ability of glycopeptides to inhibit interaction of galectin-3 with lactose

Surprisingly, it was found also that combinations of Xylose and Rhamnose with peptides can also bind specifically to Gal3 and compete with interaction of Gal3 with Lactose-HRP. Xylose-linked to the tetrapetide Xyl-ALRV (SEQ ID NO:107) compete with HRP-Lac with IC50 similar to MeGal. FIG. 13 shows representative raw data from the HRP-Lac competition experiments for peptides Gal-PAPT (SEQ ID NO:105) and Xyl-ALRV (SEQ ID NO:107). The competitive activity is quantified as decrease in color development by HRP-lac conjugate bound to Galectin-3 coated at 10 μg/ml concentration on polystyrene 96-well plates. Conjugate Rha-IWVR (SEQ ID NO:108) was 400 times more potent inhibitor for Galectin-3 binding of HRP-Lac conjugate, than the control MeGal and 10 times better than Lactose control. This activity was in the same order of the LNT, which was reported that binds to Galectin-3 with a Kd of 97 nanomolars.

Figure 14C:
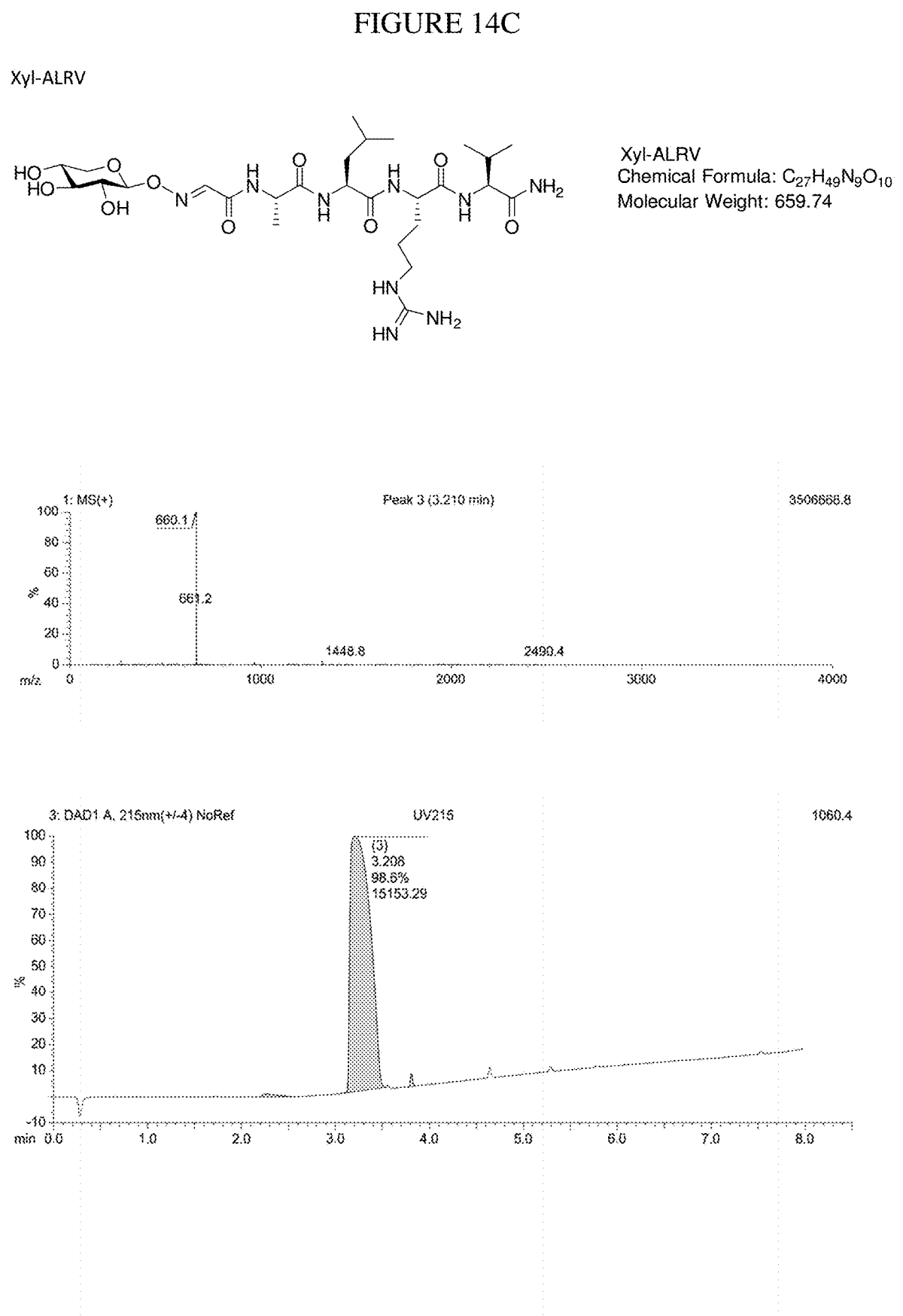

FIG. 14 shows chemical structures and characterization of glycan-peptide conjugates: FIG. 14A is Rha-IWVR (SEQ ID NO:108), FIG. 14B is Xyl-ALRV (SEQ ID NO:107), FIG. 14C is Glu-SIYG (SEQ ID NO:106), FIG. 14D is Gal-PAPT (SEQ ID NO:105).

REFERENCES

Chen, S.; Bertoldo, D.; Angelini, A.; Pojer, R; Heinis, C. *Angewandte Chemie-International Edition* 2014, 53, 1602.

Schlippe, Y. V. G.; Hartman, M. C. T.; Josephson, K.; Szostak, J. W. *JACS* 2012, 134, 10469.

Scott, J. K.; Smith, G. P. *Science* 1990, 249, 386.

Brenner, S.; Lerner, R. A. *PNAS* 1992, 89, 5381.

Santoso, B.; Lam, S.; Murray, B. W.; Chen, G. *Bioorganic & Medicinal Chemistry Letters* 2013, 23, 5680.

Kawakami, T.; Ishizawa, T.; Fujino, T.; Reid, P. C.; Suga, H.; Murakami, H. *Acs Chemical Biology* 2013, 8, 1205.

Josephson, K.; Hartman, M. C. T.; Szostak, J. W. *JACS* 2005, 127, 11727.

Jafari, M. R.; Deng, L.; Kitov, P. I.; Ng, S.; Matochko, W. L.; Tjhung, K. F.; Zeberoff, A.; Elias, A.; Klassen, J. S.; Derda, R. *ACS Chem Biol* 2014, 9, 443.

Heinis, C.; Rutherford, T.; Freund, S.; Winter, G. *Nature Chemical Biology* 2009, 5, 502.

Matochko, W. Chu, K.; Jin, B.; Lee, S. W.; Whitesides, G. M.; Derda, R. *Methods* 2012, 58, 47.

Ng, S.; Lin, E.; Kitov, P. I.; Tjhung, K. F.; Gerlits, O. O.; Deng, L.; Kasper, B.; Sood, A.; Paschal, B. M.; Zhang, P.; Ling, C. C.; Klassen, J. S.; Noren, C. J.; Mahal, L. K.; Woods, R. J.; Coates, L.; Derda, R. *J. Am. Chem, Soc.* 2015, 137, 5248-5251.

Guillon, R.; Pagniez, F.; Giraud, F.; Crépin, D.; Picot, C.; Le Borgne, M.; Morio, F.; Duflos, M. Logé, C.; Le Pape, P. *Chem Med Chem* 2011, 6, 816-825.

Kitov, P. I.; Vinals, D. F.; Ng, S.; Tjhung, K. F.; Derda, R. *J. Am. Chem. Soc.* 2014, 136, 8149-8152.

Kim, Y. W.; Grossmann, T. N.; Verdine, G. L. *Nature protocols* 2011, 6, 761-771.

Ng, S.; Jafari, M. R.; Matochko, W. L.; Derda, R. *ACS Chem Biol* 2012, 7, 1482-1487.

Matochko, W. L.; Cory Li, S.; Tang, S. K.; Derda, R. *Nucleic Acids Res.* 2014, 42, 1784-1798.

Wang, W.; Kitova, E. N.; Klassen, J. S. *Anal. Chem.* 2003, 75, 4945-4955.

Kitova, E. N.; El-Hawiet, A.; Schnier, P. D.; Klassen, J. S. *J. Am. Soc. Mass. Spectrom.* 2012, 23, 431-441.

El-Hawiet, A.; Kitova, E. N.; Klassen, J. S. *Biochemistry* 2012, 51, 4244-4253.

Sun, J.; Kitova, E. N.; Wang, W.; Klassen, J. S. *Anal. Chem.* 2006, 78, 3010-3018.

Chilkoti, A.; Tan, P. Stayton, P. S. *Proc. Natl. Acad. Sci. U.S.A.* 1995, 92, 1754-1.758.

Green, N. M. *Methods Enzymol.* 1990, 184, 51-67.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

STATEMENT REGARDING THE ELECTRONIC FILING OF A SEQUENCE LISTING

A sequence listing in ASCII text format, submitted under 37 C.F.R. § 1.821, entitled PPCT27325_ST25.TXT, 32,187 bytes in size, generated on Apr. 20, 2017, and filed electronically via EFS-Web, is provided in lieu of a paper copy. The Sequence Listing is incorporated herein by reference into the specification for its disclosures.

The embodiments of the invention in which an exclusive property or privilege is claimed are defined as follows:

1. A method for genetic encoding of chemical modifications in genetically encoded libraries of chemically modified peptides expressed on a genetically encoded display system, comprising the steps of:

(a) producing multiple peptides expressed on a genetically encoded display system with different chemical modifications, wherein said multiple peptides have identical amino acid sequences but different genetic sequences due to the presence of a silent barcode region in genetic sequences that produce identical transcriptional products, wherein the genetically encoded display system that encode different silent barcode regions are produced separately, wherein identical peptides expressed on the genetically encoded display system that encode different silent barcode regions are modified by different chemical modifications, (b) repeating step (a) by producing a peptide with a different amino acid sequence in a region encoding a peptide variable region compared to the peptide amino acid sequence produced in step (a), wherein the peptide with a different amino acid sequence produced in step (b) has a substantially similar amino acid sequence compared to the amino acid sequence of the peptide produced in step (a), (c) repeating step (b) multiple times, and (d) pooling the peptides with different chemical modifications expressed on the genetically encoded display system produced in steps (a), (b) and (c) to create a library in which the peptide amino acid sequences can be determined by genetic sequencing of the region encoding the peptide variable region and the modification can be determined by genetic sequencing of the silent barcode region.

2. The method of claim 1, wherein different peptides with a different amino acid sequences are generated by random mutagenesis.

3. The method of claim 1, wherein each of the different chemical modifications of said multiple peptides have identical amino acid sequences comprise introducing a different small molecule at any amino acid residue in the peptide.

4. The method of claim 3, wherein the chemical modifications of introducing a different small molecule at any amino acid residue in the peptide comprise site-specific chemical conjugation.

5. The method of claim 4, wherein the small molecule is a carbohydrate, biotin, or sulphonamide.

6. The method of claim 4, wherein the chemical modification is formation of oxime at the N-terminal serine or alkylation of cysteine.

7. The method of claim 1, wherein the chemical modifications are chemical reactions that insert one or more linkers, one or more cross-linkers or one or more chemical staples to convert a peptide into a macrocycle with one of more bridges.

8. The method of claim 4, wherein the small molecule is a diastereomer or enantiomer.

9. The method of claim 1, wherein the chemical modifications are enzymatic modifications.

10. The method of claim 1, wherein genetically encoded display system is phage, mRNA, ribosome, bacteria, or yeast.

11. The method of claim 1 wherein the identical transcriptional product is a peptide linker.

12. The method of claim 11 wherein the peptide linker comprises an amino acid sequence as set forth in SEQ ID NO: 10, or is encoded by a nucleotide sequence as set forth in any one of SEQ ID NOs: 11, 12, 13, 14, 15, or 16.

13. The method of claim 11 wherein the genetic barcodes do not reside within hamming distance Hd=1 from each other.

14. The method of claim 13 wherein the genetic barcodes are Hd=2 or Hd=3 away from each other.

* * * * *